(12) United States Patent
Miller et al.

(10) Patent No.: US 7,999,440 B2
(45) Date of Patent: Aug. 16, 2011

(54) MICRO-FABRICATED DEVICES HAVING A SUSPENDED MEMBRANE OR PLATE STRUCTURE

(75) Inventors: Michael Miller, Hollis, NH (US); Brett P. Masters, Watertown, MA (US)

(73) Assignee: BioScale, Inc., Lexington, MA (US)

( * ) Notice: Subject to any disclaimer, the term of this patent is extended or adjusted under 35 U.S.C. 154(b) by 1236 days.

(21) Appl. No.: 11/604,645

(22) Filed: Nov. 27, 2006

(65) Prior Publication Data
US 2008/0121611 A1  May 29, 2008

(51) Int. Cl.
*H01L 41/08* (2006.01)
(52) U.S. Cl. .................. 310/324; 310/328; 310/338
(58) Field of Classification Search .................. 310/324, 310/328, 338
See application file for complete search history.

(56) References Cited

U.S. PATENT DOCUMENTS

| | | | |
|---|---|---|---|
| 5,129,262 A | 7/1992 | White et al. | 73/599 |
| 5,189,914 A | 3/1993 | White et al. | 73/599 |
| 5,216,680 A | 6/1993 | Magnusson et al. | 372/20 |
| 5,332,469 A * | 7/1994 | Mastrangelo | 216/2 |
| 5,454,904 A | 10/1995 | Ghezzo et al. | 216/13 |
| 5,490,034 A | 2/1996 | Zavracky et al. | 361/283.4 |
| 5,501,893 A | 3/1996 | Laermer et al. | 428/161 |
| 5,565,625 A | 10/1996 | Howe et al. | 73/514.16 |
| 5,605,598 A | 2/1997 | Greiff | 156/630.1 |
| 5,725,729 A | 3/1998 | Greiff | 156/657.1 |
| 5,760,305 A | 6/1998 | Greiff | 73/514.15 |
| 5,919,364 A * | 7/1999 | Lebouitz et al. | 210/321.84 |
| 5,969,250 A | 10/1999 | Greiff | 73/514.38 |
| 6,192,757 B1 | 2/2001 | Tsang et al. | 73/514.32 |
| 6,223,598 B1 | 5/2001 | Judy | 73/514.32 |
| 6,257,059 B1 | 7/2001 | Weinberg et al. | 73/504.16 |
| 6,388,789 B1 | 5/2002 | Bernstein | 359/198 |
| 6,433,401 B1 | 8/2002 | Clark et al. | 257/524 |
| 6,506,620 B1 | 1/2003 | Scharf et al. | 438/52 |
| 6,673,694 B2 | 1/2004 | Borenstein | 438/411 |
| 6,688,158 B2 | 2/2004 | Cunningham et al. | 73/24.06 |
| 6,778,908 B2 | 8/2004 | Martorana et al. | 702/9 |
| 6,790,775 B2 | 9/2004 | Fartash | 438/667 |
| 6,837,097 B2 | 1/2005 | Cunningham et al. | 73/24.06 |

(Continued)

FOREIGN PATENT DOCUMENTS

DE     103 55 572 A1    7/2005

(Continued)

OTHER PUBLICATIONS

Chapman, Glenn et al., "Bi/In Thermal Resist for Both Si Anisotropic Wet Etching and Si/SiO₂ Plasma Etching" Presented at SPIE Micro04, Photonics West, Micromachining and Microfabrication Process Technology IX, v. 5342, (12 pages).

(Continued)

*Primary Examiner* — Thomas M Dougherty
(74) *Attorney, Agent, or Firm* — Proskauer Rose LLP

(57) ABSTRACT

The invention relates to micro-fabricated devices having a suspended membrane or plate structure and micro-fabrication techniques for making such devices. A substrate defines a cavity passing through the substrate, and the cavity defines a first opening. An intermediate portion is disposed over the substrate and defines a second opening. The second opening is larger in size than the first opening, and the dimensions of the second opening are controlled according to a parameter associated with performance of the device. A membrane is positioned adjacent the second opening.

22 Claims, 13 Drawing Sheets

U.S. PATENT DOCUMENTS

| | | | |
|---|---|---|---|
| 6,851,297 B2 | 2/2005 | Cunningham et al. | 73/24.06 |
| 6,870,624 B2 | 3/2005 | Hobbs et al. | 356/416 |
| 6,887,391 B1 | 5/2005 | Daneman et al. | 216/2 |
| 6,946,314 B2 | 9/2005 | Sawyer et al. | 438/50 |
| 6,951,715 B2 | 10/2005 | Cunningham et al. | 435/4 |
| 6,990,259 B2 | 1/2006 | Cunningham | 385/12 |
| 7,000,453 B2 | 2/2006 | Cunningham et al. | 73/24.06 |
| 7,023,544 B2 | 4/2006 | Cunningham et al. | 356/326 |
| 7,070,987 B2 | 7/2006 | Cunningham et al. | 435/287.1 |
| 7,074,311 B1 | 7/2006 | Cunningham | 204/450 |
| 7,094,595 B2 | 8/2006 | Cunningham et al. | 435/287.2 |
| 7,101,660 B2 | 9/2006 | Cunningham et al. | 435/4 |
| 7,109,633 B2 | 9/2006 | Weinberg et al. | 310/313 B |
| 7,118,710 B2 | 10/2006 | Cunningham | 422/82.09 |
| 7,142,296 B2 | 11/2006 | Cunningham et al. | 356/326 |
| 7,148,964 B2 | 12/2006 | Cunningham et al. | 356/326 |
| 7,153,702 B2 | 12/2006 | Lin et al. | 436/518 |
| 7,158,230 B2 | 1/2007 | Cunningham et al. | 356/326 |
| 7,162,125 B1 | 1/2007 | Schulz | 385/37 |
| 7,170,599 B2 | 1/2007 | Cunningham et al. | 356/326 |
| 7,175,980 B2 | 2/2007 | Qiu et al. | 435/4 |
| 7,197,198 B2 | 3/2007 | Schulz et al. | 385/12 |
| 7,202,076 B2 | 4/2007 | Cunningham et al. | 435/287.2 |
| 7,217,574 B2 | 5/2007 | Pien et al. | 436/164 |
| 7,264,973 B2 | 9/2007 | Lin et al. | 436/518 |
| 7,292,336 B2 | 11/2007 | Cunningham et al. | 356/326 |
| 7,298,477 B1 | 11/2007 | Cunningham et al. | 356/326 |
| 7,300,803 B2 | 11/2007 | Lin et al. | 436/518 |
| 7,301,628 B2 | 11/2007 | Cunningham et al. | 356/326 |
| 7,306,827 B2 | 12/2007 | Li et al. | 427/264 |
| 7,309,614 B1 | 12/2007 | Baird et al. | 436/518 |
| 7,312,090 B2 | 12/2007 | Lin et al. | 436/518 |
| 7,400,399 B2 | 7/2008 | Wawro et al. | 356/328 |
| 7,410,811 B2 | 8/2008 | Lin et al. | 436/526 |
| 2002/0067106 A1 | 6/2002 | Sunwoo et al. | 310/330 |
| 2003/0010745 A1 | 1/2003 | Field | 216/2 |
| 2003/0012693 A1 | 1/2003 | Otillar et al. | 422/58 |
| 2003/0194710 A1 | 10/2003 | Yang | 435/6 |
| 2004/0043615 A1 | 3/2004 | Yamamoto et al. | 438/689 |
| 2004/0065638 A1 | 4/2004 | Gogoi | 216/2 |
| 2004/0159629 A1 | 8/2004 | Busta | 216/22 |
| 2004/0175300 A1 | 9/2004 | Indermuhle et al. | 422/102 |
| 2004/0197931 A1 | 10/2004 | Indermuhle et al. | 436/514 |
| 2005/0045276 A1 | 3/2005 | Patel et al. | 156/345.43 |
| 2005/0064619 A1 | 3/2005 | Chavan et al. | 438/52 |
| 2005/0082944 A1 | 4/2005 | Thompson et al. | 310/318 |
| 2005/0089924 A1 | 4/2005 | Ho et al. | 435/7.1 |
| 2005/0148147 A1 | 7/2005 | Keating et al. | 438/299 |
| 2005/0157096 A1* | 7/2005 | Truninger et al. | 347/71 |
| 2006/0286685 A1 | 12/2006 | Miller et al. | 436/526 |
| 2008/0121042 A1 | 5/2008 | Miller et al. | 73/649 |

FOREIGN PATENT DOCUMENTS

| | | | |
|---|---|---|---|
| JP | 05-029633 | * | 2/1993 |

OTHER PUBLICATIONS

Chen, Kuo-Shen et al., "Silicon Strength Testing for Mesoscale Structural Applications," Mat. Res. Soc. Symp. Proc. Vo. 518, (1998) pp. 123-130.

Chen, Kuo-Shen et al., "Controlling and Testing the Fracture Strength of Silicon on the Mesoscale," Journal of the American Ceramic Society, 83 [6] (2000), pp. 1476-1484.

Chen, Kuo-Shen et al., "Effect of Process Parameters on the Surface Morphology and Mechanical Performance of Silicon Structures After Deep Reactive Ion Etching (DRIE)," Journal of Microelectromechanical Systems, vol. 11, No. 3, Jun. 2002, pp. 264-275.

Hu, S. M., "Critical Stress in Silicon Brittle Fracture, and Effect of Ion Implantation and Other Surface Treatments," Journal of Applied Physics 53(5), May 1982, pp. 3576-3580.

Lin, Chung-Hsien et al., "Design and Fabrication of a Miniaturized Bulk Acoustic Filter by High Aspect Ratio Etching," J. Microlith., Microfab., Microsyst. (Jul.-Sep. 2005), vol. 4(3), pp. 033010-1-033010-7.

Milanovic, Veljko, "Multilevel Beam SOI-MEMS Fabrication and Applications," Journal of Microelectromechanical Systems, vol. 13, No. 1, Feb. 2004, pp. 19-30.

Wilson, Carol J., et al., "Fracture Testing of Bulk Silicon Microcantilever Beams Subjected to a Side Load," Journal of Microelectromechanical Systems, vol. 5, No. 3, Sep. 1996, pp. 142-150.

Yallup, Kevin, "The Application and Commercialization of SOI as a Material for Advanced Microsystems," Future Fab International, Issue 19, pp. 1-9, Available at (http://www.future-fab.com/documents.asp?grID=208&d_ID=1182, Last visited Sep. 6, 2005.

Sung-Sik Yun et al., "Fabrication of vertical optical plane using DRIE and KOH crystalline etching of (110) silicon wafer," Sensors and Actuators A 128 (2006), 387-394 (XP 5367228A).

Li, Jishan, et al., "Piezoelectric immunosensor based on magnetic nanoparticles with simple immobilization procedures", Analytica Chimica Acta, vol. 481, pp. 191-198, (2003).

\* cited by examiner

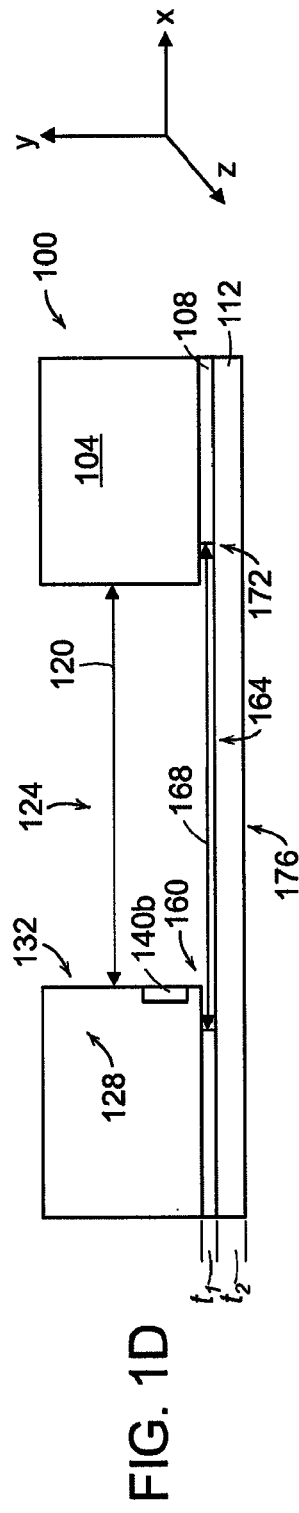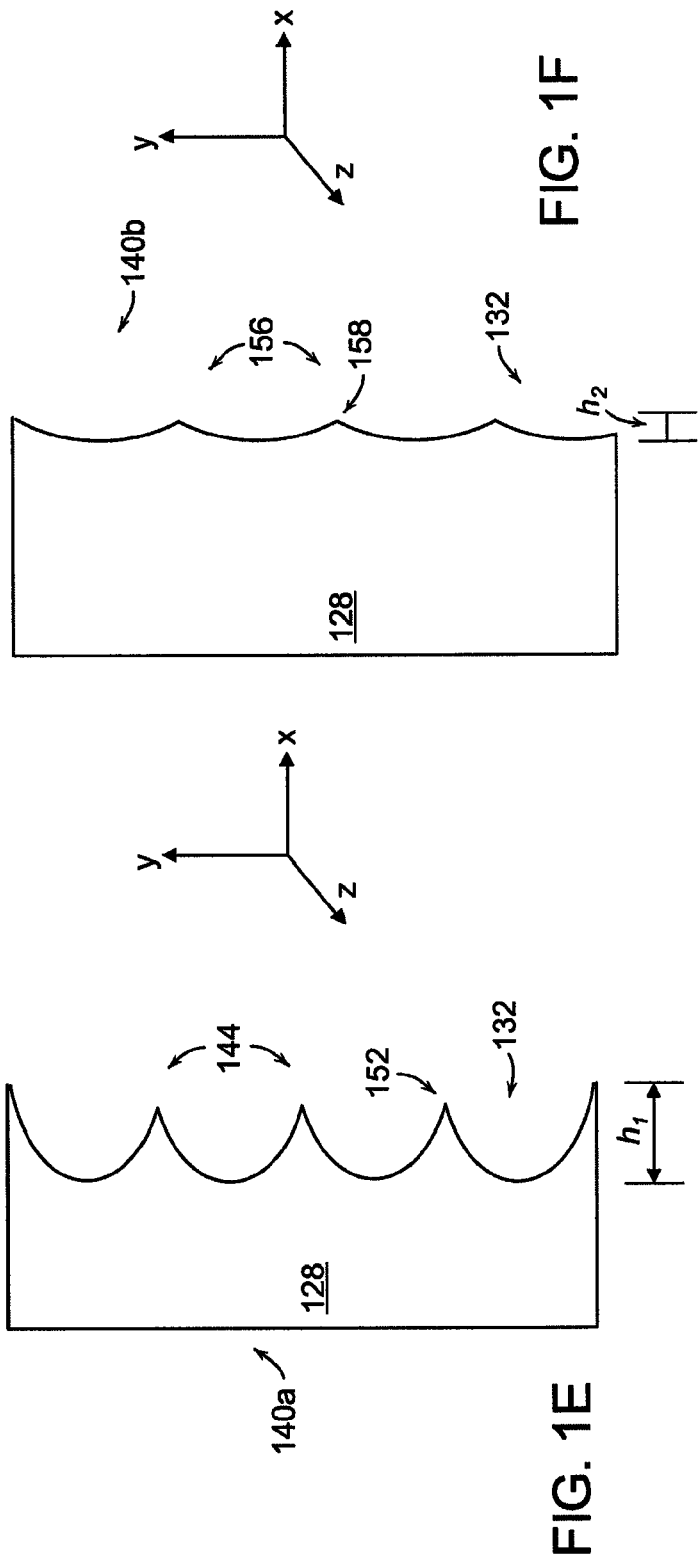

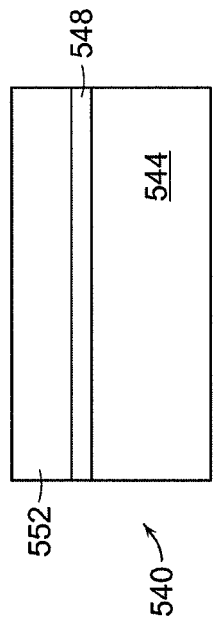
FIG. 5C
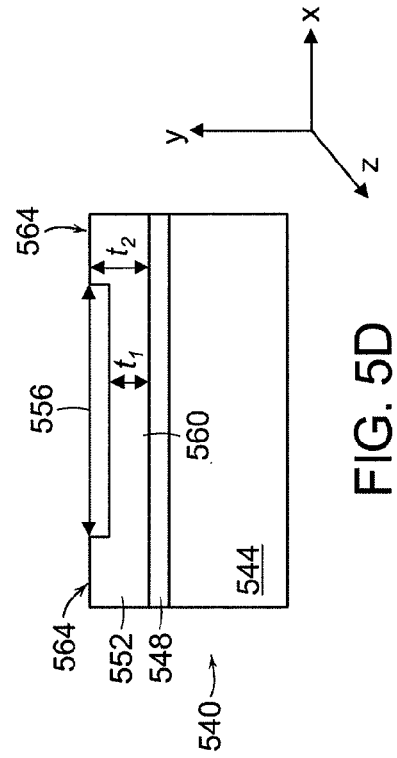
FIG. 5D
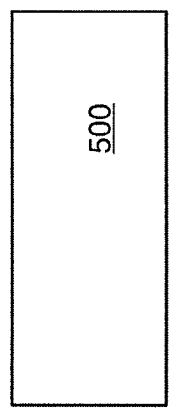
FIG. 5A
FIG. 5B

MICRO-FABRICATED DEVICES HAVING A SUSPENDED MEMBRANE OR PLATE STRUCTURE

TECHNICAL FIELD

The invention relates to materials and materials processing and more particularly to micromachining and microfabricating materials and devices.

BACKGROUND

As the size of electromechanical, electro-optical, and electronic systems shrink to micrometer and nanometer scales, components within those systems necessarily shrink as well. Smaller components require more precise processing techniques to ensure optimal system performance. Imperfections in individual components of a particular system can affect the macroscopic performance of the system and lead to failure of other components, loss of sensitivity, or loss of accuracy. Improving the operational lifetime of a particular component can be achieved by making the component and the component's interaction with the system more robust. Reducing loss of system sensitivity or loss of system accuracy can be achieved by reducing imperfections in individual components.

For example, in a micro-fabricated device employing a membrane or plate structure (collectively "membrane") suspended over a cavity, the boundary condition at the interface between the cavity and the membrane determines the robustness or lifetime of the membrane. An uneven or jagged boundary condition causes a stress concentration that can ultimately cause the membrane to fracture and fail at that boundary. When the system is exposed to or operates in a fluidic environment, the failure of the membrane can cause leakage into other components in the system. Leakage can lead to costly contamination or damage to the entire system.

A poorly designed and/or poorly fabricated boundary condition between the cavity and the membrane of an acoustic device can produce a device having a disadvantageous frequency response (e.g., low Q, low signal-to-noise ratio, or a high modal overlap and spillover). A disadvantageous frequency response is one where it is difficult to distinguish between frequency modes of the device. A disadvantageous frequency response also affects the measurement capabilities of the device by reducing the value of quality ("Q factor" or "Q") or the loss of the system. The Q of a system generally compares the time constant for decay of an oscillating physical system's amplitude to the oscillation period. Alternatively, Q compares the frequency at which a system oscillates to the rate at which the system dissipates energy. In some cases, Q is defined as the ratio between the resonant frequency of a system and the bandwidth of frequencies ($\Delta f$) over which the energy in the system is greater than half the peak value.

A subset of acoustic devices is known as resonant devices. Resonant devices have one or more resonant frequencies. The resonant frequencies of resonant devices depend on the Q factor of the resonant device. In some embodiments, standing waves associated with operation of the membrane of the resonant device are used for sensing and actuating purposes. Acoustic devices also include a family of resonant devices known as flexural plate wave ("FPW") devices. The problems discussed above also occur in FPW devices.

Additionally, imperfections in the cavity walls as a result of limitations of fabrication methods can affect the performance of the system. For example, when a cavity wall has a rough surface, introduction of a fluid to the cavity can erode the wall and cause portions of the wall to break or flake off and accumulate on the membrane as debris. The debris supplies a load on the membrane. In cases where the membrane is a sensor, the debris on the membrane can potentially result in a spurious signal and can affect the sensitivity of the device. In the case of a sensor or actuator, debris on the membrane can interfere with or change the interaction of the device with the fluid.

Furthermore, a rough cavity wall can lead to incomplete wetting of the wall, which can lead to formation of bubbles of trapped gas along the wall. A relatively rough cavity wall provides multiple sites for bubble formation or gas nucleation. As fluid flows over the cavity wall, bubbles can dislodge from the nucleation sites and move toward the membrane. The interaction of bubbles with the membrane affects the membrane's interaction with the fluid, which affects the performance of the membrane as an actuator or sensor.

SUMMARY

Hence there is a need for more robust micro-machined devices having suspended membranes or plate structures. There is also a need for micro-machined devices employing fluid paths that reduce the impact on the fluid flowing through the path. There is also a need for methods for fabricating such devices.

The methods and systems described herein include features that result in improved performance of micro-machined devices, including improved membrane or plate structure performance and longer lifetime for the devices. Devices employing the methods and systems described herein also demonstrate improved frequency response and hence improved Q. The improved Q improves the ability to distinguish between different frequency modes of the device. Additionally, devices employing these methods provide improved response to fluid property changes. Devices employing these methods also demonstrate reduced excitation of higher-order breadth-wise modes (also referred to as width-wise) of the membrane. A further advantage is improved resonance quality of observable modes (e.g., increased resolution of resonance peaks in measured signals). A further advantage of devices embodying the invention involves decreased variability and/or improved consistency of the signal output of one or more resonant devices when the devices are operated in fluidic environments. Decreased variability of signal output leads to improved ability to determine or detect changes in fluid properties when used in fluid measuring or sensing applications.

These advantages were achieved by improving the boundary condition between the membrane and the cavity over which the membrane is disposed. The improved boundary condition results in part from forming a second opening, larger in size than the opening defined by the cavity (also referred to herein as an "undercut"). The membrane is disposed over the second opening. Unlike previous devices which included a variable or uneven boundary condition, the boundary condition produced according to embodiments described herein results in straighter and/or smoother edges or ends of the membrane. In a fluidic environment in which the boundary condition is wetted, the boundary acts as a non-reflective acoustic boundary in the fluid. Fluid disposed near the boundary can act as a "squeezed fluid" and thus result in small jets of fluid mass moving into and out of the space between the membrane and the substrate (e.g., the undercut). The jets of fluid mass provide a load on the membrane that affects structural response and fluid response near the boundary condition.

The membrane can be formed from deposition of a single layer of material or from deposition of multiple layers of the same or different materials. Another feature of the concepts described herein involves improving fluid flow through a fluid path by reducing the roughness associated with a surface along which the fluid flows. More particularly, the number and/or size of gas nucleation sites in a fluidic device are reduced by using a first removal process to form the path and a second removal process to clean or polish the path prior to the introduction of any fluid, thereby improving the wettability of the surface. A smoother surface also facilitates the application of coatings to improve the hydrophilicity of the surface and improve surface wetting properties. Debris is less likely to accumulate on the membrane as a result of using two removal processes.

The invention, in one aspect, relates to a method of forming a portion of a fluid path in an etchable material. The method involves forming a cavity with a first dry removal process in a substrate material to produce a first surface of the cavity. The first surface of the cavity is associated with a first roughness. The method also involves etching the first surface of the cavity with a second wet removal process to produce a second roughness associated with the first surface of the cavity. The second roughness is generally smoother than the first roughness. The method involves applying a coating or multiple coatings to the first surface of the cavity to produce a second surface of the cavity. A coating or multiple coatings can modify a chemical property of the first surface to produce a more hydrophilic surface. In some embodiments, the second surface of the cavity features improved hydrophilicity relative to the first surface. In some embodiments, the second surface of the cavity is more wettable than the first surface of the cavity. In some embodiments, the second surface of the cavity includes gas nucleation sites that are fewer in number, smaller in size, or both relative to the first surface of the cavity.

In some embodiments, the method involves producing the second roughness according to a desired parameter associated with the performance of a micro-fabricated device. Such parameters can include improved fluid flow through the device or improved susceptibility of surfaces of the device to chemical treatment. In some embodiments, the first dry removal process, the second wet removal process or both include an anisotropic etching process. In some embodiments, forming the cavity involves an alternating sequence of passivation and etching.

The fluid path can form a portion of a fluid chamber or a fluid channel. In some embodiments, forming the cavity involves forming one or more sidewalls having an angle of between about 85° and about 95° relative to a vertical axis defined by the cavity. The etchable material can include silicon, and forming the cavity can involve deep reactive ion etching. The second wet removal process can involve using a silicon etchant for producing the second roughness. Examples of silicon etchants include isotropic etchants, such as mixtures of hydrofluoric acid, nitric acid, acetic acid and water, or mixtures of nitric acid, ammonium fluoride and water or anisotropic etchants, such as potassium hydroxide, sodium hydroxide, ammonia hydroxide, tetramethylammonia hydroxide, hydrazine, or combinations thereof. In some embodiments, the duration of etching the first surface of the cavity is between about 2 and about 60 minutes.

In some embodiments, the cavity defines a first opening adjacent an intermediate layer disposed over the substrate material. The method can involve etching through the intermediate layer with a third removal process to define a second opening adjacent the substrate. The second opening is larger than the first opening. The third removal process can involve using an isotropic etchant. In some embodiments, the third layer includes silicon oxide, and the third removal process involves using a hydrofluoric acid, a buffered hydrofluoric acid, a buffered oxide etchant, or any combination thereof.

In some embodiments, etching the first surface of the cavity to produce the second roughness improves the wettability of the first surface of the cavity. Etching the first surface of the cavity can reduce in number or in size one or more gas nucleation sites in the first surface of the cavity. Etching the first surface of the cavity can involve hindering debris associated with the first roughness from engaging a membrane or plate structure that cooperates with the cavity to form the fluid path. In some embodiments, etching the first surface of the cavity involves improving the hydrophilicity of the surface of the cavity. In some embodiments, forming the cavity involves forming two sets of parallel walls to form a rectangular cavity. Cavities of other geometries are also within the scope of the invention. In some embodiments, an electroactive layer is disposed on a surface of the membrane and a set of electrodes are disposed on a surface of the electroactive layer. The electroactive layer can be a piezoelectric material, for example, aluminum nitride.

In some embodiments, applying the coating to produce the second surface of the cavity improves wettability. In some embodiments, where the coating partially covers the first surface of the cavity, wettability of the device is improved. In some embodiments, applying the coating to produce the second surface of the cavity facilitates or accomplishes biofunctionalization of the device, for example, by facilitating attachment of biological molecules to the second surface.

The invention, in another aspect, features a micro-fabricated device. The device includes a substrate defining a cavity passing through the substrate. The cavity defines a surface to form a portion of a fluid path. The device includes a coating applied to the surface of the cavity. The device includes a membrane that defines a first surface and a second surface. The second surface cooperates with the cavity to form a portion of the fluid path. The surface of the cavity is produced by a first dry removal process that is associated with a first roughness. The first roughness is reduced by a second wet removal process to define a second roughness.

In some embodiments, the second roughness includes an average size variation in a direction normal to the surface of the cavity of less than about 3 micrometers. The membrane can be associated with a wave defining an oscillation having a spatial wavelength, and the second roughness can include an average size variation in a direction normal to the surface of the cavity of about 3 to about 10 percent of the spatial wavelength.

The cavity can include a length dimension between about 10 micrometers and about 10,000 micrometers. The cavity can include a depth dimension between about 100 micrometers and about 1,000 micrometers. In some embodiments, the membrane includes a thickness dimension between about 0.1 micrometers and about 20 micrometers. The device can include an intermediate layer disposed between the substrate and the membrane. The intermediate layer can include an etch stop material to hinder the first or second removal processes, or both from affecting the second surface of the membrane. In such embodiments, the intermediate layer can include a thickness dimension of between about 0.1 micrometers and about 10 micrometers.

In some embodiments, a first thickness dimension of the intermediate layer is determined at least in part on a second thickness dimension of a layer of an interaction between a fluid and the membrane. The second thickness is measured in a direction normal to the first or second surface of the membrane.

In some embodiments, the micro-fabricated device includes at least one of an acoustic sensor, a viscosity sensor, a density sensor, a mass sensor, or any combination thereof. The micro-fabricated device can be a flexural plate wave ("FPW") device. The wet removal process, the coating, or both can reduce in number or in size one or more gas nucleation sites in at least one of the surface of the cavity, the coating, or both. In some embodiments, the wet removal process, the coating, or both hinder debris associated with the first roughness from engaging the membrane. The substrate can include silicon, and the first dry removal process can involve deep reactive ion etching. The wet removal process or the coating can reduce contamination of a fluid in the fluid path. In some embodiments, the wet removal process or the coating can improve the wettability of one or more surfaces of the cavity.

The invention, in another aspect, features a micro-fabricated device. The device includes a first means for forming a cavity in a substrate material to define a surface. The surface is associated with a first roughness. The device also includes a second means for reducing the first roughness to define a second roughness associated with the surface. The device includes a membrane cooperating with the cavity to form a portion of a fluid path.

The invention, in one aspect, features a micro-fabricated device. The device includes a substrate defining a first cavity passing through the substrate. The cavity defines a first opening. An intermediate portion is disposed over the substrate and defines a second opening that is larger in size than the first opening. The size of the second opening is controlled according to a parameter of the device. The dimensions of the second opening are determined when the second opening is defined. The device includes a membrane that is positioned adjacent the second opening.

The dimensions of the second opening can include lateral dimensions (e.g., length and/or width) and vertical dimensions (e.g., height). In some embodiments, the intermediate portion is formed by an intermediate layer disposed on the substrate material. The intermediate layer can include an oxide material. In some embodiments, the intermediate portion is formed by the membrane. The membrane can include at least one of silicon, polysilicon, silicon nitride, aluminum nitride, zinc oxide, aluminum, molybdenum, copper, gold, titanium, parylene, PMMA, SU-8, or any combination thereof. In some embodiments, the membrane includes two or more layers including one or more membrane materials.

The size of the second opening can be greater than the size of the first opening by an amount greater than about a thickness of the intermediate portion. In some embodiments, the second opening is larger in size than the first opening by an amount greater than about two times a thickness of the intermediate portion. The second opening can be larger than the first opening by an amount between about 5 and about 10 micrometers. In some embodiments, the second opening is larger than the first opening by an amount between about 10 micrometers and about 30 micrometers. In some embodiments, the intermediate portion has a thickness of about 1 micrometer.

The size (e.g., the length and width) of the membrane can be determined based at least in part on the size of the second opening. In some embodiments, the membrane cooperates with the second opening to form a boundary associated with a boundary condition, and the size of the membrane is determined at least in part by the boundary condition. The membrane can be a plate structure. In some embodiments, the device includes an electroactive layer disposed on a surface of the membrane and a set of electrodes disposed on a surface of the electroactive layer. The electroactive layer can be a piezoelectric material, for example, aluminum nitride. In some embodiments, the cavity cooperates with the membrane to form a fluid path. In some embodiments, the parameter of the device includes sensitivity, accuracy, operational lifetime, or any combination of these. In some embodiments, the parameter of the device includes frequency response.

The invention, in another aspect, relates to a method for making a micro-fabricated device. The method involves forming a cavity to define a first opening through a substrate material with a first removal process. The method also involves forming a second opening adjacent the first opening in a first layer disposed on the substrate material with a second process. The second opening is larger in size than the first opening, and the dimensions of the second opening are controlled according to a parameter associated with performance of the device.

In some embodiments, the method involves disposing a membrane material on the first layer. Disposing the membrane material on the first layer can involve disposing a portion of the membrane material on the substrate material. The membrane material can be, for example, silicon, silicon nitride, polysilicon, or any combination thereof. Some embodiments involve forming the second opening in the first layer by removing substantially all of the first layer from the substrate material.

The first removal process can involve etching. The second process can involve etching a portion of a sacrificial layer disposed between the substrate material and the first layer (e.g., when the first layer is a membrane material). In some embodiments, the second process involves depositing a sacrificial material on the substrate to approximately define the second opening and depositing the first layer on both the sacrificial material and the substrate material. The sacrificial material is removed with a removal process.

Forming the second opening can involve isotropically etching the first layer. In some embodiments, the duration of isotropic etching is based on the desired size of the second opening and an etch rate of the isotropic etching process.

The invention, in another aspect, relates to a method for making a micro-fabricated device. The method involves forming a cavity to define a first opening through a substrate with a first removal process and forming a second opening relative to a membrane material with a second process. The method involves disposing the second opening over the first opening. The second opening is larger in size than the first opening, and the dimensions of the second opening are controlled according to a parameter associated with performance of the device.

In some embodiments, the second opening is formed in the membrane material by a second removal process. The second removal process can involve anisotropic etching of the membrane material. Some embodiments involve disposing the second opening over the first opening by bonding a surface of the membrane material to a corresponding surface of the substrate material. Such bonding can include, for example, anodic or fusion bonding.

In some embodiments, the second opening is formed by depositing a gap material on the membrane material via, for example, chemical vapor deposition, physical vapor deposition, molecular beam epitaxy, or any combination thereof. In such embodiments, disposing the second opening over the first opening comprises bonding a portion of the gap material to the substrate material.

The invention, in another aspect, features a micro-fabricated device. The device includes a substrate defining a cavity passing through the substrate and defining a first opening. The device also includes an intermediate portion that defines a second opening adjacent the first opening. The device includes a means for controlling the size of the second opening when the second opening is defined. The dimensions of the second opening are controlled according to a parameter associated with performance of the device. A membrane is disposed adjacent the second opening.

The details of one or more examples are set forth in the accompanying drawings and the description below. Further features, aspects, and advantages of the invention will become apparent from the description, the drawings, and the claims.

BRIEF DESCRIPTION OF THE DRAWINGS

FIG. 1D is a schematic cross-sectional illustration of a cavity in an etchable material after a first removal process.

FIG. 1E is an expanded view of a portion of the cavity wall of FIG. 1C illustrating a roughness profile after formation of the cavity.

FIG. 1F is an expanded view of a portion of the cavity wall of FIG. 1D illustrating a roughness profile after a second removal process.

FIG. 5A is a schematic cross-sectional illustration of a wafer.

FIG. 5B is a schematic cross-sectional illustration of a cavity in the wafer of FIG. 5A.

FIG. 5C is a schematic cross-sectional illustration of a second wafer.

FIG. 5D is a schematic cross-sectional illustration of the wafer of FIG. 5C after an opening has been formed.

DETAILED DESCRIPTION

Figure 1A:
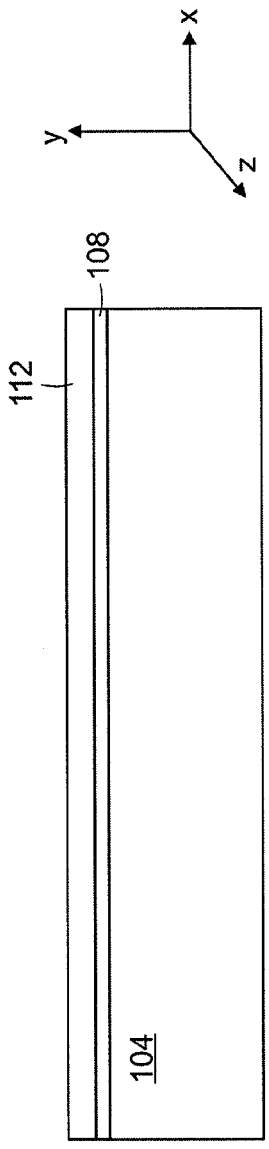
FIG. 1A is a schematic cross-sectional illustration of an etchable material.

FIGS. 1A-1D illustrate steps for forming a fluid path in an etchable material. Referring to FIG. 1A, a wafer 100 includes a substrate material 104, an intermediate layer 108 disposed on the substrate material 104, and a membrane layer 112 disposed on the intermediate layer 108. In general, the substrate 104 is a material that can be etched. Examples of suitable substrate materials include, for example, silicon, glasses, dielectric materials, metals, or materials suitable for laser micromachining. In some commercial applications, it is desirable to form a fluid path in the etchable material (e.g., in the substrate 104).

Figure 1B:
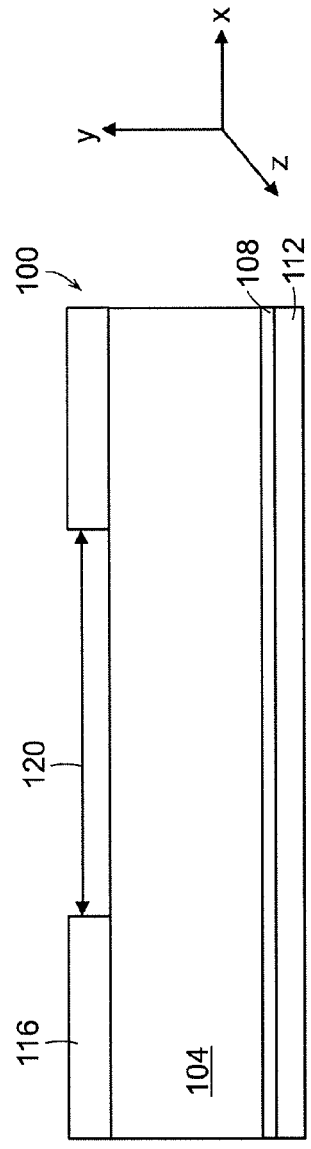
FIG. 1B is a schematic cross-sectional illustration of a step for forming a fluid path in the etchable material of FIG. 1A.

FIG. 1B shows the wafer 100 rotated in the plane of the page by 180° such that the intermediate layer 108 and the membrane 112 are positioned below the substrate 104. A photoresist material 116 is applied to the substrate 104 (e.g., by spinning the photoresist material 116 on to the substrate 104). The photoresist material 116 is patterned to define an opening 120. The opening 120 defines a geometric shape (in the x-z plane) that will define the material to be subsequently removed from the substrate 104. The size of the opening 120 along the x-axis and the z-axis can be between about 10 micrometers and about 10,000 micrometers depending on the particular application for the wafer 100. In some embodiments, the opening 120 is rectangular in shape. The opening 120 can also have circular, elliptical, or irregular geometry.

Figure 1C:
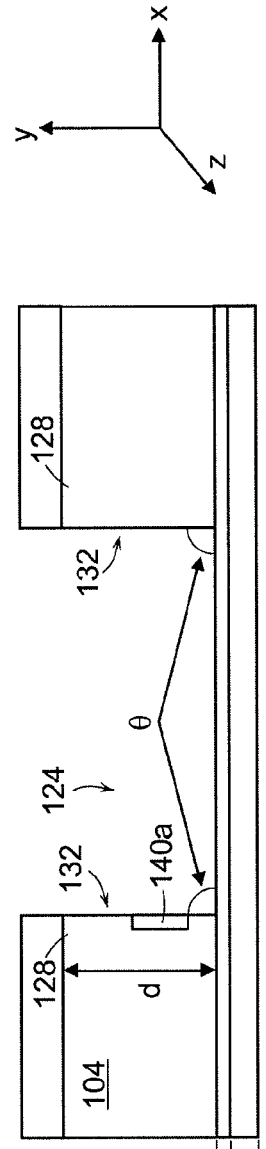
FIG. 1C is a schematic cross-sectional illustration of a cavity in an etchable material.

After the photoresist material 116 is patterned, the wafer 100 is subjected to a dry removal process to produce a cavity 124 as depicted in FIG. 1C. The cavity 124 includes walls 128 defined by the substrate material 104 which are exposed after the dry removal process. The walls 128 includes a surface 132 associated with a first roughness. The dry removal process can involve a deep reactive ion etching process. Deep reactive ion etching is a highly anisotropic etch that is used to create relatively high-aspect ratio holes (e.g., cavities with substantially vertical walls 128 relative to the y-axis). Deep reactive ion etching generally involves either cryogenic wafer processing or the "Bosch process," both of which are known to those of skill in the art. An advantage of deep reactive ion etching processes includes improved control over the geometry of a relatively deep cavity 104 (e.g., a cavity having a depth d greater than about 100 micrometers). Improved control over the geometry of the cavity 104 results from the deep reactive ion etching process involving a sequence of alternating etching and passivating steps. Deep reactive ion etching process is a well-known process, an example of which is further described in detail in U.S. Pat. No. 5,501,893, which is assigned to Robert Bosch GmbH. The walls 128 form an angle θ with the intermediate layer 108. The angle θ is depicted as substantially a right angle, but other angle values are possible, for example, between about 85° and about 95° (e.g., a trapezoidal geometry). The angle θ and the straightness of the side walls are determined by the nature of the dry removal process. Dry etching processes other than deep reactive ion etching can yield a wider range of wall angles and degree of straightness. In some embodiments, the intermediate layer 108 is an etch stop layer. The etch stop layer prevents the dry removal process from contacting or otherwise removing material from the membrane 112. For example, the intermediate layer 108 can be formed of a material that is not susceptible to removal by the dry removal process. The material properties of the intermediate layer 108 prevent the dry removal process from removing material from the membrane 112 even if the intermediate layer 108 is not an etch stop layer, but is merely a sacrificial layer.

The depth d of the cavity is measured along the y-axis in a direction normal to the intermediate layer 108, the membrane 112, or both. In some embodiments, the depth d of the cavity is between about 100 micrometers and about 1,000 micrometers, depending on the particular application for the wafer 100. For example, the phase velocity or group velocity of a traveling wave on the membrane 112 and interacting with the fluid can be influenced by the dimensions of the cavity 104. In addition, the wavelength or period of the wave can be influenced by boundary conditions imposed by the cavity 104, the intermediate layer 108, and/or the membrane 112. In this embodiment, the depth d of the cavity is relatively large (compared to, for example, the thickness $t_2$ along the x-axis of the membrane 112). To achieve a relatively large depth d, removal processes with a relatively high etch rate and a relatively high selectivity to the surrounding structures are preferred.

Referring now to FIG. 1D, in embodiments including an intermediate layer 108, the intermediate layer 108 defines a first thickness $t_1$ of between about 0.1 and about 10 micrometers measured along the y-axis. The thickness $t_i$ of the intermediate layer 108 may be selected based on a thickness (not shown) of a layer of fluid that interacts with the membrane 112 during operation. The second opening 168 defined by the intermediate layer 108 defines an edge 172 of the membrane 112. The edge 172 of the second opening may be smoother than the boundary 160 of the first opening, which can result in improved performance. For example, a smoother edge 172 can improve the robustness of the membrane 112 and can result in less excitation energy correlated with width-wise, higher order, modes. This result is evidenced in the observed pass band as more energy focused into the length-wise, low order breadth-wise modes of the membrane 112. Length-wise modes refer to modes observed along the longer of two lateral edges of the membrane 112 (depicted along the x-axis in FIG. 1D), and breadth-wide modes refer to modes observed along the shorter of two lateral edges of the membrane (depicted along the z-axis in FIG. 1D). Depending on the geometry of the membrane 112, the length-wise and/or breadth-wise modes may be oriented along different axes than those depicted in FIG. 1D without departing from the concepts described herein.

When operating in a gaseous environment, the gap produced by the second opening 168 possibly results in squeeze film/loading with gas being forced in and out of the gap, towards the cavity 124 during resonant motion of the membrane 112. This mechanism also favors energy in lower order breadth-wise modes, which correlate along the length of the membrane 112 to give higher residues in the length-wise, low order breadth-wise resonant modes.

In some embodiments, the size of the undercut is defined by the size of the second opening 168. The dimensions of the second opening can include lateral dimensions (e.g., along the x-axis and z-axis) and vertical dimensions (e.g., along the y-axis) as well as other coordinate systems (e.g., cylindrical coordinates). The size of the second opening 168 is related to the dimensions of the second opening 168, and the dimensions of the second opening 168 are determined during formation of the second opening 168 as discussed herein (e.g., by a removal or deposition process). Generally, the dimensions of the second opening 168 are controlled and/or determined based on a desired performance of the wafer 100 operating in a device.

When operating in a liquid environment, additional advantages are realized by the use of an undercut and are evidenced by the response of the fluid-membrane 112 coupled device. For example, the boundary 160 of the cavity 124 and in the second opening 168 when wetted can result in a non-reflective acoustic boundary for the fluid (not shown). In some embodiments, the thickness $t_1$ of the intermediate layer 108 is approximately 1 micrometer and the thickness of the fluid interaction layer (not shown) is approximately 8 micrometers. Fluid interaction layer refers to a portion of the fluid that is affected by the dissipation of acoustic energy from the membrane. Both the thickness $t_1$ of the intermediate layer 108 and the thickness of the fluid interaction layer are relatively small compared to the depth d of the cavity 124. The relative sizes of the intermediate layer 108, the interaction layer and the cavity 124 can lead to a "squeezed fluid" loading effect that results from small quantities of fluid mass that are forced into and out of the gap between the membrane 112 and the substrate 104. Both the thickness $t_1$ of the intermediate layer 108 and the size difference between the first opening 120 and the second opening 168 (discussed further below with respect to FIG. 1D) can affect the performance of a fluid-membrane coupled device.

The membrane 112 defines a second thickness $t_2$ of between about 0.1 micrometers and about 20 micrometers measured along the y-axis. The thickness $t_1$ of the intermediate layer 108 and the thickness $t_2$ of the membrane 112 can be changed to vary the performance or sensitivity of a device (not shown). It will be appreciated that the embodiments described hereafter that generally include a substrate, an intermediate layer or intermediate portion, and a membrane each can define depth, length, and thickness dimensions along the x-axis, z-axis, and y-axis respectively having similar values as described herein.

In some embodiments, the dry removal process (depicted in FIG. 1C) involves an etching process. Etching can involve removal with a chemical etchant, with a laser, or by ion bombardment. The dry removal process can also include ablation techniques, for example, vaporization, chipping, or other erosive processes. In some embodiments, the dry removal process includes isotropic or anisotropic etching. In general, isotropic etching involves directionally-independent removal of the substrate material 104 using, for example, a chemical substance. More particularly, isotropic etchants attack a material in all directions at substantially the same rate. To the extent that substrate 104 has a crystal lattice structure, isotropic etchants are not constrained by that crystal structure.

In some embodiments, the dry removal process includes an alternating sequence of etching and passivation. A portion of the substrate 104 is removed during the etching step with an etchant (not shown). The etchant is then removed, and a passivating substance (not shown) is provided to the portion of the substrate remaining after etching. The passivating substance, for example a polymer or polymer residue, serves to protect the portion of the surface 132 of the wall 128 that has already been etched from being further etched by the etchant as the depth of the cavity (along the y-axis) is increased with subsequent etchings. In this way, the geometry of the cavity 124 (e.g., the combination of the walls 128 and the angle θ) can be more accurately controlled.

After the dry removal process forms the cavity 124, the surfaces 132 of the cavity walls 128 are associated with or exhibit a first roughness. Additionally, a polymer or polymer residue (not shown) for passivation may still be present on the surfaces 132. FIG. 1E illustrates an expanded view of across section 140a of a cavity wall 128 and a surface 132 of FIG. 1C. The cross section 140a illustrates representative features of the surface 132 after the dry removal process and exemplifies the first roughness produced after the dry removal process. A series of residual imperfections 144 spaced along the y-axis remain after the dry removal process. The imperfections 144 (also sometimes observed as and referred to as scallops or scalloping) are associated with a height $h_1$ measured along the x-axis normal to the y-axis. These features can vary as a function of depth d along the etched cavity 124 wall (along the y-axis). Additionally, other imperfections can be produced as a result of the etching process (e.g., imperfections displaying a different cross-sectional geometry than those depicted in FIGS. 1E and 1F). Reducing the effect of other these other types of imperfections are also within the scope of the concepts described herein. The imperfections 144 can include concave locations between peaks 152 as well as the peaks 152 themselves that protrude from the surface 132 of the cavity walls 128. Other types of imperfections 144, sometimes called inclusions (not shown) or protrusions of differing geometry or uniformity from the imperfections 144 depicted in FIGS. 1E and 1F are fairly common results during removal processes. Imperfections 144 on the cavity walls 128 near the boundary 160 (e.g., at the bottom of the cavity 124) can directly affect the boundary conditions, and hence operation, of the membrane 112.

In some embodiments, the height $h_1$, as measured from a peak 152 of the imperfection 144 to the deepest point along the x-axis is between about 5 and about 10 micrometers. The imperfections 144 can be observed using surface height scans, for example, using scanning electron microscopy, atomic force microscopy or a surface profilometer scan. The roughnesses of the surface 132 can be quantified using, for example, an Ra value. The Ra value represents the ratio of the average roughness of the surface 132 per unit length or area. The Ra value is calculated by integrating the absolute deviation of height $h_1$ from the mean height (not shown), measured over a given length (e.g., d) or area during a surface profilometer scan, and then dividing the integrated value by the value of the length or area, respectively, over which the scan occurred.

Referring to FIG. 1E, in a fluidic environment, gas bubbles (not shown) tend to become trapped and/or nucleate at the sites of the imperfections 144. Because the peaks 152 interface with the fluid, heterogeneous nucleation can occur. Gas bubbles tend to affect fluid flow along the surface 132 and thereby affect performance of the membrane 112. For example, an oscillation (not shown) can be established in the membrane 112 along the y-axis. The oscillation can be, for example, a traveling wave or a standing wave in an excited resonant mode. In some embodiments, the wavelength of the excited mode of the oscillation is about 38 micrometers. Therefore, an imperfection 144 height $h_1$ of about 5 to 10 micrometers is between about 13-27% of this wavelength distance. An imperfection 144 height $h_1$ of this magnitude affects the performance of the membrane 112 and affects the oscillation by causing interference effects and degrading the performance of the membrane 112.

A wet removal process is used to reduce the value of the height $h_1$ of the imperfections 144 and/or remove the polymer residues from the surface 132 of the wall 128. The wet removal process produces a second roughness illustrated in a second cross-section 140b of FIGS. 1D & 1F. In one embodiment, the wet removal process involves anisotropically etching the surface 132 of the wall 128. In general, the second roughness is produced to satisfy or in accordance with a desired parameter that is associated with performance of the device. The cross-section 140b (illustrated in FIG. 1F) illustrates features of the surface 132 after the wet removal process and depicts the second roughness produced after the wet removal process. A series of residual imperfections 156 spaced along the y-axis remain after the wet removal process. These imperfections 156 are associated with a height $h_2$ measured along the x-axis. In general, the height $h_2$ is less than the height $h_1$ of the imperfections 144 after the dry removal process. In some embodiments, the height $h_2$ is less than about 3 micrometers. In some embodiments, the height $h_2$ is less than about 10% of the wavelength on the membrane 112. In some embodiments, the height $h_2$ is between 3-10% of the wavelength distance.

In some embodiments, the imperfections 156 are eroded versions of the imperfections 144 where the depth has been reduced along the x-axis and the distance along the y-axis between peaks 158 has been increased. In contrast to the imperfections 144 of cross-section 140a after the dry removal process, the cross-section 140b of FIG. 1F illustrates smaller imperfections 152 (e.g., the peaks 158 are smaller along the x-axis). As a result, the cross-section 140b features smaller sites for gas bubbles to become trapped and nucleate when a device incorporating the wafer 100 is operated in a fluidic environment. Less gas bubble nucleation leads to improved wettability of the surfaces 132 of the cavity 124 walls 128. Improved wettability generally leads to improved fluid flow along the walls 128, which improves the sensitivity of the device.

Furthermore, a fluid flowing along the surface 132 of the wall 128 can cause portions of the imperfections 144 of the cross-section 140a to break off more easily. The fluid tends to overcome the structural strength of a peak 152 of a particular imperfection 144 because the relatively large value of $h_1$ reduces structural strength of the peak 152 in a direction along the y-axis. Broken off portions of these peaks 152 form debris (not shown) that is carried by the fluid toward the membrane 112. Some of the debris is deposited by the fluid on the membrane 112. Debris can have several detrimental effects. In general, debris can interfere with the operation of the membrane 112 by locally changing the structural properties of the device and fluid environment. For a sensor application, the added material on the membrane 112 can reduce the membrane's sensitivity or complicate calibration of the device. For example, if debris comes in contract with the membrane 112 after calibration of the device, a spurious signal can be produced as a result of the debris. Moreover, when debris is initially present but only weakly bound to the membrane 112 and subsequently leaves the surface of the membrane 112 during the operational life of the device a spurious signal can again result.

The wet removal processes can involve using an anisotropic etchant. In general, anisotropic etchants are directionally-dependent and are constrained by the crystal structure of the substrate 104. Referring to FIGS. 1C and 1D, in some embodiments, an anisotropic etchant can be chosen based on desired features of the cavity 124, such as cavity depth d or the angle θ between the walls 128 and the intermediate layer 108. In some embodiments, the wet removal process includes using a silicon etchant, for example, potassium hydroxide, sodium hydroxide, ammonia hydroxide, tetramethylammonia hydroxide, or hydrazine. The duration of the wet removal process can be between about 2 and about 60 minutes.

Experimental results have demonstrated the feasibility and desirability of using the wet removal process after formation of the cavity 124 using the dry removal process. In one embodiment, potassium hydroxide was used as the anisotropic etchant for the wet removal process producing the second roughness in a silicon substrate 104 having a <100> crystal orientation (e.g., crystal planes oriented parallel to the y-z plane). The imperfections 144 (shown in FIG. 1E) on the wall 132 were reduced as discussed above, and the <111> plane of the silicon substrate 104 was exposed at the bottom of the cavity 124 (e.g., near the boundary 160) after approximately 10 minutes of etching (e.g., appearing as a diagonal in the x-y plane). The etch rate was approximately 0.5 micrometers/minute, as estimated by the change in the size of the cavity 124 opening 120 along the x-axis. Examination of the cavity 124 and the membrane 112 using a surface height scan illustrated the reduced roughness features on the surface 132 of the wall 128. In some embodiments, a wet etchant consisting of potassium hydroxide in a concentration of 20% the weight of water, etching at 80° C. for 5 minutes can be used to produce the desired second roughness, thereby improving performance of the device.

Referring to FIG. 1D, in some embodiments, the wet removal process creates a more well-defined boundary condition at a boundary 160 between the wall 128 of the cavity 124 and the intermediate layer 108. In some embodiments, the boundary 160 occurs between the wall 128 and the membrane 112. The boundary 160 is fixed relative to the membrane 112 or intermediate layer 108 such that increasing the duration of the wet removal process does not substantially remove the membrane 112 or intermediate layer 108 in the proximity of the boundary 160. Instead, the crystal plane of the substrate 104, e.g., the <111> plane, is exposed.

In some embodiments, the second wet removal process improves the susceptibility of the surface 132 to chemical treatment. In general, the surface 132 is easier to chemically modify after the wet removal process. More particularly, a chemical coating (not shown) can be applied to the surface 132, and a metal (not shown) can be deposited on the chemical coating. In the cross section 140a after the dry removal process, the chemical coating cannot be uniformly applied to the surface 132 because inclusions in the surface and protrusions from the surface mask the deposition process. For example, the peaks 152 (e.g., the height variations $h_1$ of the peaks 152) limit uniform application of the chemical coating on the imperfections 144 between the peaks 152. After the wet removal process, the height $h_2$ of the peaks 158 has been reduced, and the chemical coating can be more uniformly applied to the surface 132. The surface 132 depicted in cross section 140b of FIG. 1F is generally easier to wet than the surface 132 depicted in cross section 140a of FIG. 1E. Additionally, the surface in FIG. 1F is likely to result in decreased bubble nucleation after wetting. In addition, a coating (not shown) can be more uniformly applied to the surface 132 depicted in FIG. 1F than that of FIG. 1E. The coating applied to the surface (not shown) of the cavity improves fluid flow through the cavity 104 or performance of a device employing the wafer 100.

For example, when the substrate material 104 is a silicon material or glass material, a silane material can be applied as a coating to the surface 132. A silane material refers to a family of chemical compounds that can be used to link chemical groups to silicon or glass surfaces (e.g., the surface 132). Chemical compounds in the silane family include compounds having a silicon atom and which can be terminated with a chemical group and/or an alcohol group that can be cross-linked to form a stable layer. An example of a chemical compound from the silane family is 3-aminopropyltriethoxysilane. Generally, the substrate material will include groups that can bond to the alcohol group of the silane. Compounds in the silane family can bond to the surface 132 and act as a hydrophilic coating, facilitate linking a hydrophilic layer or to facilitate biofunctionalization of a device employing the wafer 100. Compounds in the silane family allow the surface 132 to be further modified because molecules of the compounds include a chemical end group (e.g., amine group) to which other chemical components can be linked. In some embodiments, the added molecules include hydrophilic groups such as ethylene glycol units to produce a hydrophilic and more easily wettable surface. In other embodiments biomolecules such as antibodies can be linked to these surface layers using well-known biochemical techniques. Other coatings that improve the hydrophilicity or wettability of the surface 132 can be used and will be apparent to those of skill in the art to, for example, improve fluid flow over the surface 132 and in the cavity 104. Such coatings are useful for applications of the cavity 104 or surface involving an aqueous environment. In some embodiments, a silane coated surface 132 is hydrophobic and can be used for applications involving organic materials to provide good wetting with these fluids.

In certain embodiments, the hydrophilic material is one or more of a surfactant, a polymeric hydrocarbon, or an amphipathic protein. In certain embodiments, the hydrophilic surface is characterized by a water contact angle of less than about 90°. The surfactant can be, for example, Tergitol, NP40, Triton X-100, Tween® 20, Tween® 40, Tween® 65, TWEEN® 80, Tween® 85, 3-[(3-Cholamidopropyl)dimethylammonio]-1-propanesulfonate, 2,4,7,9-Tetramethyl-5-decyne-4,7-diol ethoxylate, MERPOL® OJ, MERPOL® SE, or MERPOL® SH. In other embodiments, the polymeric hydrocarbon can be, for example, polyethylene glycol, poly(ethylene glycol) methyl ether, ethylene glycol monosalicylate, di(ethylene-d8-glycol), di(ethylene glycol)2-ethylhexyl ether, di(ethylene glycol) benzyl ether, di(ethylene glycol-d2), or di(ethylene glycol) hexyl ether. In still other embodiments, the amphipathic protein can be albumin, ovalbumin, serum albumin, oleosins, gelatin, or casein. In further embodiments, the hydrophilic material can be, for example, polypropylene, polystyrene, doped polystyrene, polycarbonate, PTFE, ULTEM® or PET.

In some embodiments, a metal coating can be applied to the surface 132 of the substrate 104. Examples of metals coatings include gold, silver, nickel, chromium or titanium or a combination of these materials. The thickness in the x direction of the coating can be approximately 1,000 Angstroms or 100 nanometers. Thicker layers—several thousand Angstroms thick—are also common. A molecule including a thiol group (or a sulfhydryl group) containing a sulfur atom and a hydrogen atom can be bonded to the metal coating. These thiol-terminated molecules can have hydrophilic groups. In some embodiments, a thiol-coated surface 132 is hydrophobic and can be used for applications involving organic materials to provide good wetting with these fluids. In some embodiments, a coating (not shown) is applied to one or more surfaces 164, 176 of the membrane 112. The coating on the membrane 112 can improve performance of the membrane or device in a similar manner as that discussed above for the cavity walls 128 (e.g., by improved wettability, reduced debris, or improved flow properties).

While the dry and wet removal processes have been described in the context of processing the wafer 100 to form a cavity 124, it will be appreciated that these processes can be used in other contexts. The use of the term "cavity" is not meant to specify a particular cross-sectional geometry or aspect ratio and generally refers to a portion of the wafer 100 that has been removed (e.g., from the substrate 104, the intermediate layer 108, or the membrane 112, where applicable). The processes described herein can be performed, for example, without a membrane 112 or intermediate layer 108. The steps described above can be used to form fluid channels or molds in an etchable material, for example, silicon. The fluid channels or molds have desired features as described above such as a second roughness that is smoother relative to the first roughness for improved fluid flow. In some embodiments, an etch stop portion or layer may be used to improve the geometrical definition of the cavity 124 (e.g., a flat floor portion between the walls 128). A coating can be applied to the fluid channels or molds to improve fluid flow as well.

In some embodiments, the intermediate layer 108 is formed of a material that is susceptible to removal by a third subsequent removal process. The third removal process can be selected to remove some or all of the intermediate layer 108 but not substantially remove additional substrate 104 material. The third removal process can be selected to remove a portion of the intermediate layer 108, exposing a bottom surface 164 of the membrane 112 to the cavity 124. The membrane 112 then cooperates with the cavity 124 to form a portion of a fluid path or a fluid chamber. In some embodiments, the third removal process involves using an isotropic etchant.

Examples of suitable etch stop materials include silicon oxide (SiO2) or silicon-germanium (SiGe) when the substrate 104 is a silicon material. Certain etchants will etch the silicon substrate 104 but not the SiO2 or the SiGe. In some embodiments, the etch-stop material can be a metal, metal alloy or a polymer material that is not susceptible to a particular removal process. The etch-stop can include a dopant, for example, phosphorous or boron. When the intermediate layer 108 includes silicon oxide, a hydrofluoric acid, a buffered hydrofluoric acid, a buffered oxide etchant, or any combination thereof can be used to remove the intermediate layer 108 or a portion thereof without removing substantial amounts of the substrate 104. Similarly, when the intermediate layer includes germanium-silicon, a hydrogen peroxide can be used to remove the intermediate layer 108 without removing substantial amounts of the substrate 104.

In some embodiments, the membrane 112 serves as an etch stop layer without the need for an intermediate layer 108. In such embodiments, the membrane 112 is similar to the intermediate layer 108 in terms of selectively allowing etching of the substrate 104 without allowing etching of the membrane 112 material. An example of an appropriate membrane 112 material that can also act as an etch stop material is silicon nitride.

In some embodiments, the third removal process includes etching through the intermediate layer 108 to define a second opening 168 that is larger in size than the first opening 120. The second opening 168 is adjacent the substrate 104 and permits the membrane 112 to cooperate with the cavity 124 to form a fluid chamber. In some embodiments, the second opening 168 is referred to as an undercut because the edge 172 between the membrane 112 and the cavity 124 is larger in size than the opening 120 in the cavity 124. The larger edge 172 relieves stress concentrations associated with points or cusps that occur where the wall 132 intersects the membrane 112 or the intermediate layer 108 (e.g., similar to the peaks 152 illustrated in FIG. 1E). When a protrusion 152 is located at the membrane 112, a stress concentration or pressure point occurs. The membrane 112 is prone to fracture at the stress concentration. The second opening 168 reduces the magnitude (size of the peak 152) and the number of stress concentration locations or the number of locations with relatively substantial stress concentrations. In embodiments in which the membrane 112 is part of a resonant device, acoustic performance is improved by the undercut 168 because the size of the protrusions 158 has been reduced. Furthermore, the membrane 112 is able to withstand greater pressure fluctuations without failure in devices employing an undercut 168 because the size of the protrusions 158 (and thereby the magnitude of the stress concentrations) have been reduced.

An exemplary description of wafer processing to create a micromachined device is described below to illustrate the types of devices that can employ features of the concepts described herein. It will be appreciated that the concepts described herein can be used in different processing applications without departing from the spirit or the scope of the invention. In some embodiments, additional microfabrication process steps can be performed on the membrane 112, and the membrane 112 is sometimes considered to be a device layer. Layers can be added to the membrane 112 by deposition as used herein throughout can be performed using techniques such as physical or chemical vapor deposition, sputtering, bonding, ion implantation, molecular beam epitaxy, or other methods. These layers can be patterned using standard photolithographic techniques that involve masking layers and etching steps. For example, the membrane 112 can be a p-type semiconductor material, having a resistivity of 4-6 ohm-centimeters and a thickness $t_2$ of about 2.2 micrometers. The top surface 176 of the membrane 112 can be modified by implantation of boron atoms (not shown). For example, a dose of about $5 \times 10^{15}/cm^2$ with energy of about 35 keV can be performed followed by rapid thermal annealing at about 1,100° C. for about 30 seconds. In other embodiments, a highly doped layer of silicon can be deposited onto the membrane 112. In other embodiments a metal layer can be deposited onto the membrane 112.

In some embodiments, reactive sputtering is used to deposit an electroactive layer or film (not shown), for example, a piezoelectric material such as aluminum nitride, on the doped membrane 112. An oxide mask (e.g., silicon dioxide) (not shown) can be deposited on the electroactive layer using, for example, chemical vapor deposition. The mask can be patterned with a photoresist material (not shown) and etched with a buffered hydrofluoric acid to form an outline of a via (not shown) to the membrane 112. The via is etched using hot phosphoric acid, and the oxide mask is stripped from the wafer 100 using buffered hydrofluoric acid. The via can be used for electrical communication with the membrane 112 (e.g., for providing an electrical signal in actuating applications or for measuring an electrical signal in sensing applications).

In one embodiment, a metal layer (not shown) is deposited on the electroactive layer (not shown). In some embodiments, two or more metals are deposited. In an embodiment having two metals, the first metal is titanium having a thickness of about 0.02 micrometers, and the second metal is gold having a thickness of about 0.08 micrometers. The metals form electrodes on the surface of the electroactive layer. The metals are patterned and etched to form, for example, interdigitated electrodes according to a desired design to produce a resonant device capable of actuating the electroactive layer and capable of sensing changes in the resonant response of the composite membrane 112. The resonant device is capable of, for example, outputting a signal that varies based on changes in physical properties of a fluid that is in contact with a surface of the resonant device. A protectant, for example, a photoresist material (not shown) can be deposited over processed surface (not shown) of the membrane 112 to protect the membrane layers from being affected by subsequent removal processes (e.g., similarly as discussed above for forming the cavity 124, reducing the roughness of the surfaces 132 of the walls 128, or for forming the second opening 160). In some embodiments, any of the above steps can be employed to form a device layer on the membrane 112.

Figure 2A:
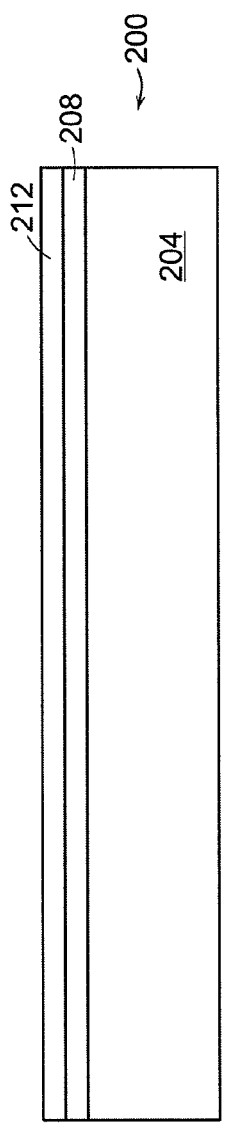
FIG. 2A is a schematic cross-sectional illustration of a wafer.
Figure 2B:
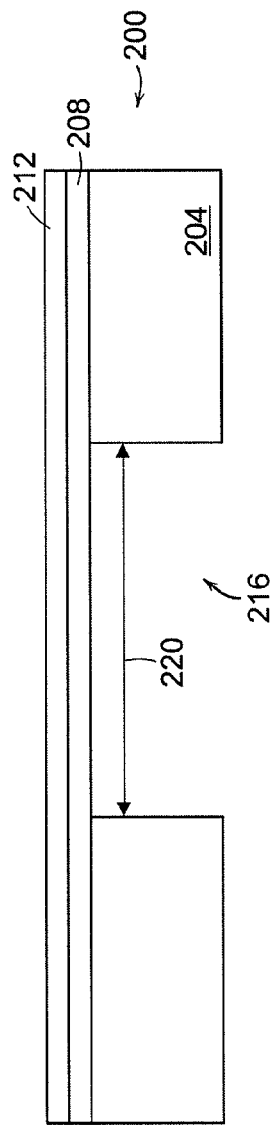
FIG. 2B is a schematic cross-sectional illustration of a cavity in the wafer of FIG. 2A.
Figure 2C:
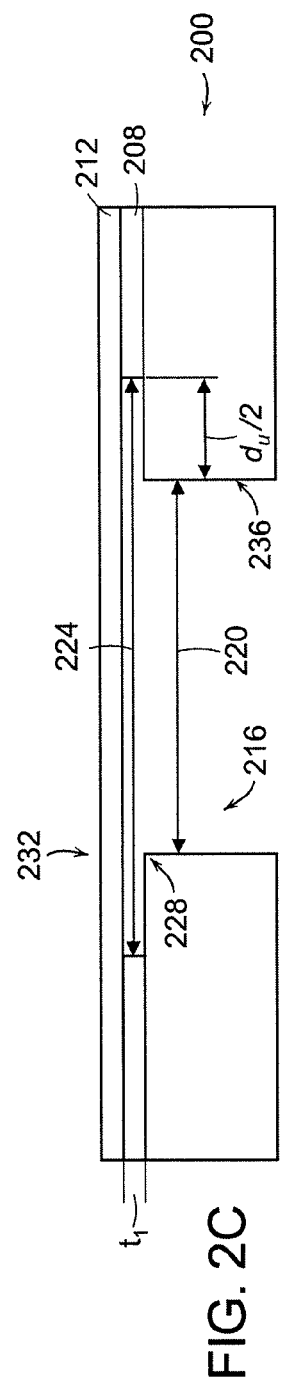
FIG. 2C is a schematic cross-sectional illustration of the wafer of FIG. 2B after removal of a portion of an intermediate layer.

FIGS. 2A-2C illustrate steps for forming a membrane over a cavity involving removal of a portion of an intermediate layer. Referring to FIG. 2A, a wafer 200 including a substrate 204, an intermediate layer 208, and a device layer 212 is illustrated and is provided as a starting material for processing the wafer 200. In some embodiments, the wafer 200 is a silicon-on-insulator ("SOI") wafer having a silicon substrate 204, an intermediate layer 208 that includes an oxide material, and a device layer 212 that includes silicon.

Referring to FIG. 2B, a cavity 216 is formed through the substrate 204, for example, using the removal processes discussed above with respect to FIGS. 1A-1F (e.g., defining an opening 220 of the cavity 216 using a photoresist material (not shown) and using subsequent dry and wet removal processes). In some embodiments, the cavity 216 is formed using one removal process, for example, a wet removal process instead of sequential dry and wet removal processes. For example, in one embodiment, the cavity 216 can be formed using a wet anisotropic etchant, for example potassium hydroxide. Other types of cavities as discussed hereafter can also be formed using a single removal process. The intermediate layer 208 acts as an etch stop to selectively prevent the removal process from affecting the device layer 212. Referring to FIG. 2C, a portion of the intermediate layer 208 is then removed using a selective removal process that removes the intermediate layer 208 without removing a substantial amount of the substrate 204 or the device layer 212. The selective removal process creates a second opening 224 that is adjacent the cavity 216 and larger in size than the first opening 220.

The size of the second opening 224 is determined and/or controlled during the selective removal process. The size of the second opening 224 can be controlled, for example, by controlling the duration of time that the selective removal process is conducted. The duration of time can be selected based on knowledge of the removal or etch rate of the specific etchant used in the selective removal process. In this way, the amount that the size of the second opening 224 exceeds the size of the first opening 220 is determined based on desired performance of a device (not shown) that employs the device layer 212. In general, as the duration of the selective removal process increases, the difference between the size of the second opening 224 and the size of the first opening 220 also increases. In some embodiments, the size of the second opening 224 exceeds the size of the first opening 220 by between about 5 micrometers and about 30 micrometers.

The geometry of a corner 228 defined by the cavity 216 and the second opening 224 is based on the removal process used to form the cavity 216 and/or the second opening 224. In some embodiments, the corner 228 appears to be concave relative to the cavity 216. In some embodiments, the corner 228 appears convex relative to the cavity 216. An advantage realized by the concepts described herein includes controllably removing a portion the intermediate layer 208 to form the second opening 224. Controllably removing a portion of the intermediate layer 208 allows the second opening 224 to define a larger size than would generally occur based on using only the selective removal process to remove the substrate material 204 and to remove the intermediate layer 208. More specifically, the selective removal process is employed for a total time duration that includes a first time period sufficient to remove the intermediate layer 208 (e.g., and expose the device layer 212 to the cavity 216) and a second time period sufficient to increase the size of the second opening 224 by a depth $d_u$ according to a desired parameter associated with performance of the device.

In general, the value of depth $d_u$ is selected based on the particular application for the device employing the wafer 200. In some embodiments, the value of the depth $d_u$ and/or the half-depth $d_u/2$ and the value of the thickness $t_1$ of the intermediate layer 208 are related to each other. For example, in one embodiment, the aspect ratio of the depth $d_u$ to the thickness $t_1$ of the intermediate layer 208 is selected to be equal to a value of 2. If the thickness $t_1$ of the intermediate layer is increased by 50%, the depth $d_u$ would also be increased by 50%. In this manner, the thickness $t_1$ can be determined based on the depth $d_u$ that is specified for a particular device or application, or vice versa (e.g., the depth $d_u$ can be determined based on the thickness $t_1$ that is specified). The depth $d_u$ and the thickness $t_1$ can be changed (e.g., increased or decreased) by integer or non-integer (e.g., fractional) multiples of the aspect ratio. The aspect ratio can be selected to be equal to values other than 2. For example, when the wafer 200 is employed in a flexural plate wave ("FPW") device, the depth $d_u$ selected is associated with the operating wavelength or resonant wavelengths used in the operation of the FPW.

In some embodiments, the size of the second opening 224 exceeds the size of the first opening 220 by an amount greater than about a thickness $t_1$ of the intermediate layer 208. In some embodiments, the size of the second opening 224 exceeds the size of the first opening 220 by an amount greater than about twice the thickness $t_1$ of the intermediate layer 208. In some embodiments, the thickness $t_1$ of the intermediate layer 208 and the dimensions or size of the second opening 224 are related to affect the performance of a device.

The embodiments herein containing the device layer 212 (or a membrane) can each include an electroactive layer (not shown) deposited on the membrane. For example, the electroactive layer can be a piezoelectric material. When an electroactive layer is employed on a membrane, a plurality of electrodes (not shown), for example, interdigitated electrodes can be deposited on the electroactive layer for performing sensing and/or actuating functions relative to the membrane. In some embodiments, the electroactive layer and electrodes are deposited on the membrane 212 before forming the cavity 204 is formed. In such embodiments, a protective layer, for example, a photoresist material (not shown) is used to protect the electroactive layer and electrodes during subsequent wafer processing (e.g., in forming the cavity 204 and smoothing the walls 236 of the cavity 204 as discussed above).

Figure 3A:
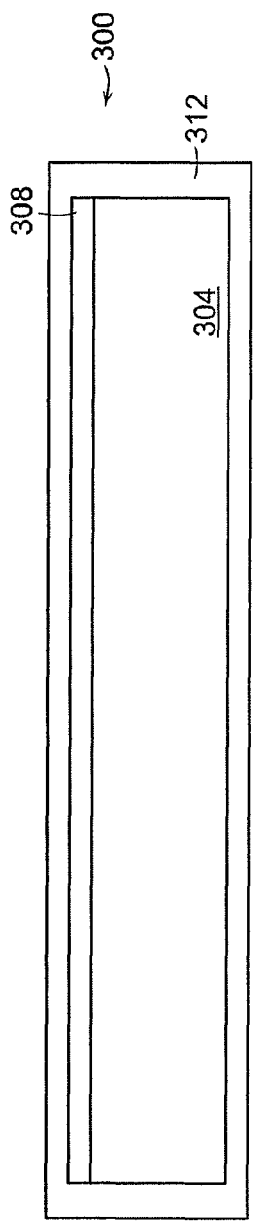
FIG. 3A is a schematic cross-sectional illustration of a wafer.
Figure 3B:
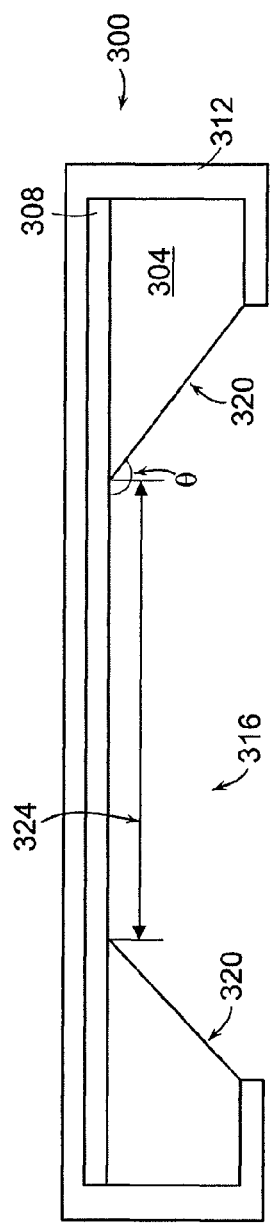
FIG. 3B is a schematic cross-sectional illustration of a cavity in the wafer of FIG. 3A.
Figure 3C:
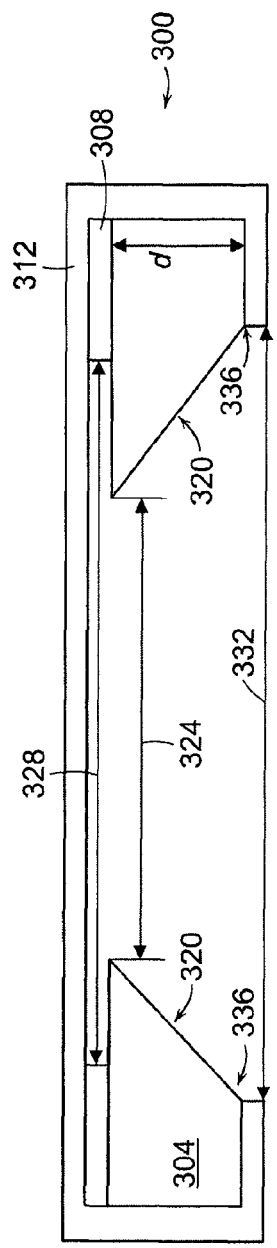
FIG. 3C is a schematic cross-sectional illustration of the wafer of FIG. 3B after removal of a portion of an intermediate layer.

FIGS. 3A-3C illustrate alternative steps for forming a membrane over a cavity involving removal of a portion of an intermediate layer. Referring to FIG. 3A, a wafer 300 is illustrated including a substrate 304, and intermediate layer 308, and a membrane material 312 that surrounds the substrate 304 and intermediate layer 308. The membrane material 312 is deposited on the wafer 300 using, for example, thin-film deposition techniques such as chemical or physical vapor deposition techniques. The membrane material 312 can be, for example, a silicon nitride material. The silicon nitride material has advantageous properties when used as a membrane material 312 and for wafer processing. For example, silicon nitride can be deposited on the wafer 300 adjacent the substrate 304 and the intermediate layer 308 in a single coating, as depicted in FIG. 3A, which reduces the number of subsequent process steps required. Silicon nitride, particularly low-stress variations of silicon nitride, works well as a membrane material and as an etch mask during formation of the cavity 316. A separate mask layer (not shown) is, therefore, not required to be deposited or patterned on the substrate 304 prior to formation of the cavity 316. The pattern can be formed directly in the silicon nitride material.

FIG. 3B illustrates the wafer 300 of FIG. 3A including the cavity 316 formed through the substrate 304 and the portion of the membrane material 312 adjacent the cavity 316. The walls 320 of the cavity 316 form an angle θ with the intermediate layer 308. The angle θ is determined based on the type of removal process used to form the cavity 316 and the type of substrate material 304 (e.g., the lattice structure of the substrate material 304). A first opening 324 is defined at the interface between the intermediate layer 308 and the cavity 316. In some embodiments, the intermediate layer 308 acts as an etch stop layer to prevent the removal processes that formed the cavity 316 from affecting the membrane material 312. In some embodiments, the intermediate layer 308 is not an etch stop, but the membrane material 312 (e.g., silicon nitride) is resistant to the removal processes that form the cavity 316. In such embodiments, structural damage to the membrane material 312 is minimized because the membrane material 312 is resistant to, for example, the chemicals using during the removal process employed to create the cavity 316. This is particularly true when a wet removal process involves potassium hydroxide to produce the cavity 316.

FIG. 3C illustrates the wafer 300 after a selective removal process has removed a portion of the intermediate layer 308 to form a second opening 328 that is greater in size than the first opening 324. As discussed above, the size of the second opening 328 is controlled during formation of the second opening 328 according to a desired parameter associated with performance of a device (not shown) employing the wafer 300. A third opening 332 defined by the cavity 316 in the substrate 304 and the membrane material 312 is greater in size than both the first opening 324 and the second opening 328. However, the interface 336 between the third opening 332 and the substrate 304 does not substantially impact performance of a device employing the wafer 300. The size of the first opening 324 is based in part on the size of the third opening 332, the angle θ of the cavity 316, and the depth d of the cavity 316.

Figure 4A:
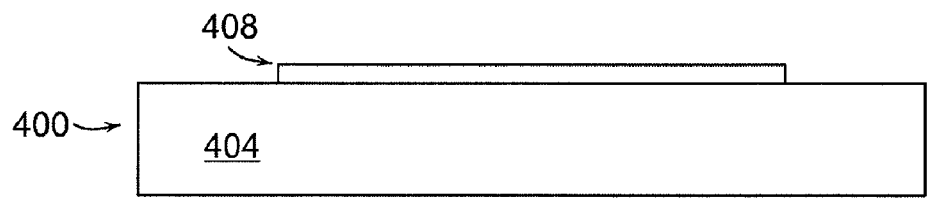
FIG. 4A is a schematic cross-sectional illustration of a wafer.

FIGS. 4A-4D illustrate alternative steps for forming a membrane over a cavity involving removal of a portion of an intermediate layer. Referring to FIG. 4A, a wafer 400 is illustrated that includes a substrate material 404 and a sacrificial layer 408. The sacrificial layer 408 is deposited on the substrate material 404. The sacrificial layer 408 is patterned to define thickness, length and width dimensions. A portion of the sacrificial layer 408 is removed to leave the patterned dimensions deposited on the substrate material 404.

Figure 4B:
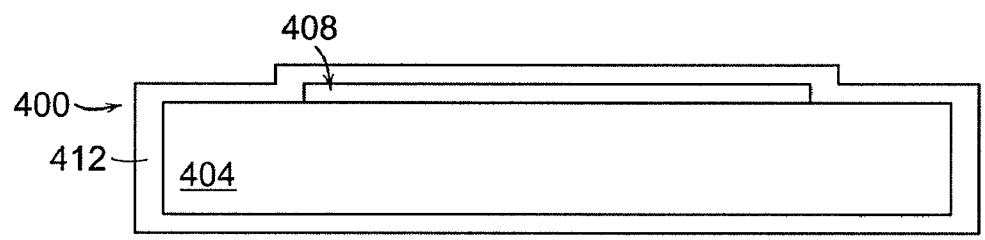
FIG. 4B is a schematic cross-sectional illustration of the wafer of FIG. 4A after deposition of a membrane material.
Figure 4C:
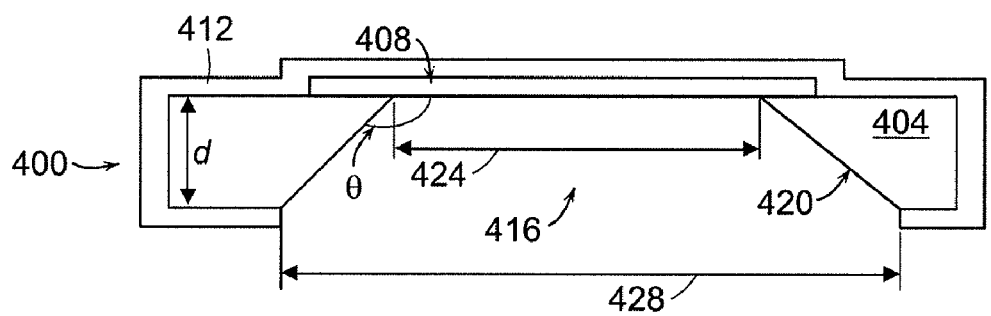
FIG. 4C is a schematic cross-sectional illustration of a cavity in the wafer of FIG. 4B.

FIG. 4B illustrates a membrane material 412 deposited over the sacrificial layer 408 and the substrate material 404. The membrane material 412 surrounds the wafer 400. In some embodiments, the configuration of FIG. 4B occurs after the membrane material 412 that includes silicon nitride is deposited on the sacrificial layer 408 and the substrate 404. FIG. 4C includes a cavity 416 through the membrane material 412 and the substrate material 404. The cavity 416 is formed using methods discussed above. The cavity 416 defines walls 420 that form an opening 424 as the interface of the walls 420 and the sacrificial layer 408. The size of the opening 424 is determined based on the type of removal process used for forming the cavity 416 and the lattice structure of the substrate material 404. More particularly, the size of the first opening 424 depends on the angle θ between the walls 420 and the sacrificial layer 408, the size of the cavity opening 428, and the depth d of the cavity.

Figure 4D:
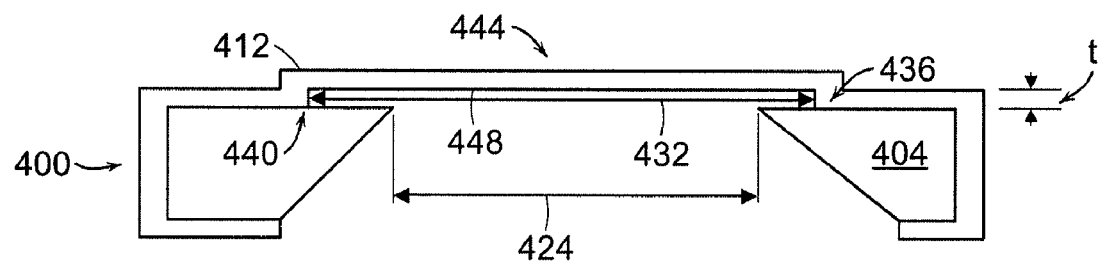
FIG. 4D is a schematic cross-sectional illustration of the wafer of FIG. 4C after removal of the intermediate layer.

FIG. 4D illustrates the wafer 400 after a selective removal process has removed the sacrificial layer 408 from the substrate material 404. The space formerly occupied by the sacrificial layer 408 defines a second opening 432 that is greater in size than the first opening 424. In this embodiment, the size of the second opening 432 is determined during deposition and/or patterning of the sacrificial layer 408 on the substrate material 404. Several advantages are realized with this embodiment. For example, the selective-removal process is self-limiting and not time-dependent. More particularly, the membrane material 412 can be chosen to be resistant to the selective removal process. The selective removal process does not affect the membrane material 412 after the sacrificial layer 408 has been removed. The duration of the selective removal process is a duration sufficiently long to remove the sacrificial layer entirely. An advantage of this embodiment includes using the selective removal process longer than this duration does not generally affect the membrane material 412. In this embodiment in particular and other embodiments generally, the size of the membrane material 412 is determined in part based on the size of the second opening 432 because the membrane 412 is suspended over the second opening 432.

Additionally, the membrane material 412 includes an intermediate portion 436 that defines a thickness t. The thickness t of the intermediate portion represents the thickness of the former sacrificial layer 408. The interface 440 between the intermediate portion 436 and the substrate material 404 defines a boundary condition between the membrane 412 and the substrate material 404. The membrane material 412 cooperates with the second opening 432 to define this boundary condition. Both the boundary condition and the thickness t are determined during deposition and/or patterning of the sacrificial layer 408. As such, the boundary condition can be determined by lithography on the front side 444 of the wafer 400 rather than on the back side 448 of the membrane material 412. Additionally, boundary condition uniformity depends more on lithography techniques than on the removal processes that form the cavity 416 (e.g., an etch through the substrate 404). In general, deposition and patterning for lithography allow greater control over geometry and dimensions than removal processes.

Figure 5E:
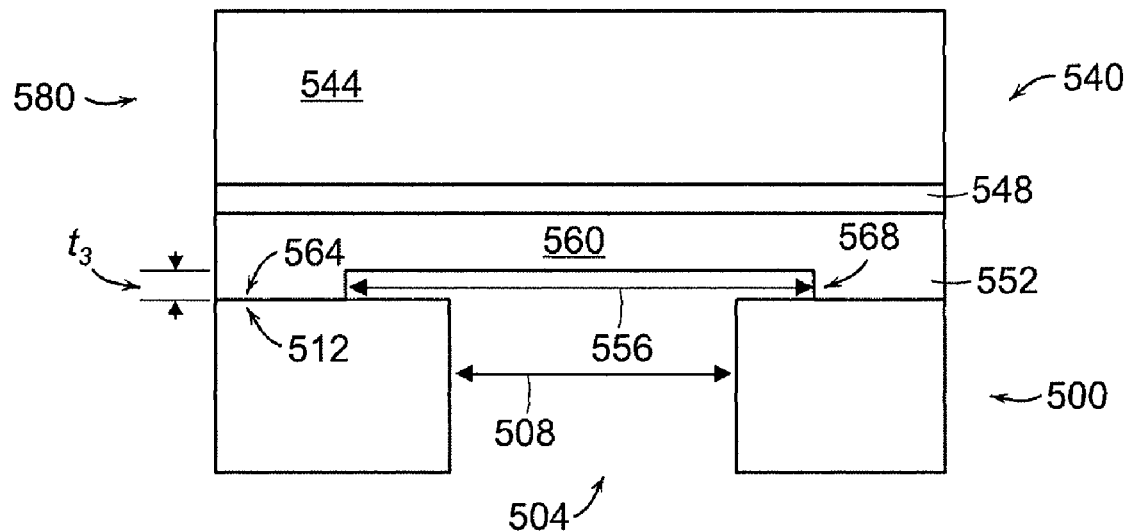
FIG. 5E is a schematic cross-sectional illustration of a composite wafer after the wafers of FIG. 5B and FIG. 5D have been bonded together.

FIGS. 5A-5F illustrate alternative steps for forming a membrane over a cavity involving bonding two layers together. Referring to FIG. 5A a first wafer 500 is illustrated. FIG. 5B illustrates the first wafer 500 after a cavity 504 has been formed through the wafer 500. The cavity 504 can be formed according to the methods described herein previously (e.g., subsequent dry and wet removal processes). The cavity 504 defines a first opening 508, and the wafer 500 defines two surfaces 512 that are prepared for bonding with another wafer. For example, the two surfaces 512 are typically prepared for bonding by a cleaning process. In an embodiment in which the first wafer 500 is made of a glass material, the preparation process can involve deposition of a metallic material (not shown) on the surfaces 512. Another material is then bonded to the metallic material rather than the glass material (e.g., the wafer 500). As illustrated, the cavity 504 is substantially rectangular; however, other geometries are possible as well, for example, the trapezoidal, circular, elliptical, or other irregular geometries described previously.

FIG. 5C illustrates a second wafer 540. The second wafer 540 includes a substrate 544, an intermediate layer 548, and a membrane layer 552. In some embodiments, the second wafer 540 is an SOI wafer.

FIG. 5D depicts the second wafer 540 after a portion of the membrane layer 552 has been selectively removed to define a second opening 556. The second opening 556 is defined by a removal process, for example, etching a portion of the membrane 552 to form a region 560 of the membrane 552 adjacent the second opening 556. The region 560 has a thickness $t_1$ that is less than the thickness $t_2$ of the entire membrane layer 552. To define the dimensions in the x-z plane of the second opening 556, a photoresist material (not shown) can be patterned on the membrane layer 552. After the selective removal process, the photoresist material is removed from the membrane layer 552 to expose a surface 564 of the membrane layer 552. The surface 564 is then prepared for bonding to the corresponding surfaces 512 of the first wafer 500. The surface 564 can be prepared for bonding by a cleaning process.

Referring to FIG. 5E, the second wafer 540 has been bonded to the first wafer 500 to form a composite wafer 580. More particularly, the surface 564 of the membrane layer 552 has been bonded to the corresponding surface 512 of the first wafer 500 by, for example, anodic or fusion bonding. As illustrated, the second opening 556 is positioned adjacent the first opening 508 when the second wafer 540 is bonded to the first wafer 500. The size of the second opening 556 is greater than the size of first opening 508. The size of the second opening 556 is determined according to a desired parameter associated with performance of a particular device in which the composite wafer 580 will be used. The size of the second opening 556 is determined during, for example, deposition of the photoresist material on the membrane layer 552, as discussed above.

The thin region 560 of the membrane layer 552 acts as a membrane structure suspended over the second opening 556, the first opening 508, and the cavity 504. Because the membrane layer 552 includes the thin region 560 that acts as a membrane structure, the membrane layer 552 also includes an intermediate portion 568 that has a thickness defined as $t_3 = (t_2 - t_1)$. The thickness $t_3$ of the intermediate portion 568 can define approximate thicknesses as discussed above for intermediate layers. For example, the thickness $t_3$ can be approximately the depth of the fluid interaction between the thin region 560 and the fluid. The intermediate portion 568 and the thin region 560 of the membrane layer 552 perform similar functions as a separate intermediate layer and membrane.

Figure 5F:
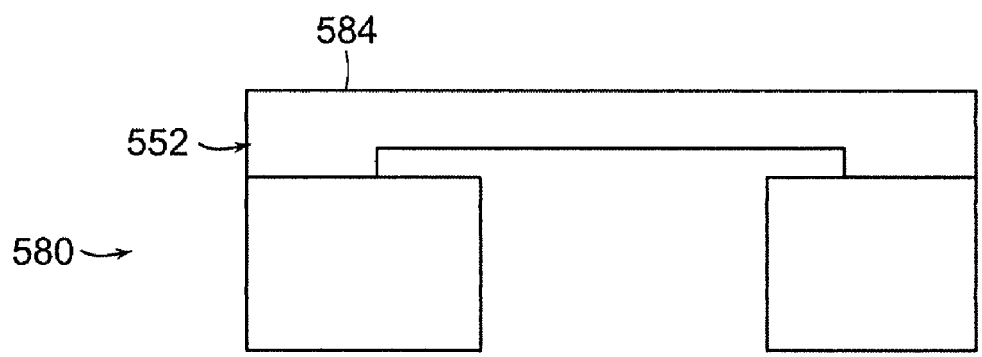
FIG. 5F is a schematic cross-sectional illustration of the composite wafer of FIG. 5E after a portion of the wafer of FIG. 5D has been removed.

FIG. 5F depicts the composite wafer 580 after the substrate 544 and the intermediate layer 548 have been removed. In some embodiments, the substrate 544 is removed with a first removal process, for example, a dry or wet removal process. If the substrate 544 material is silicon, the dry removal process can be a deep reactive ion etching process. The intermediate layer 548 can be removed with a second removal process, for example, a dry or wet removal process as discussed above. The second removal process can generally be chosen to avoid or minimize surface damage to the membrane layer 552, in particular, to the surface 584 of the membrane layer 552 that is exposed after the intermediate layer 548 has been removed. The composite wafer 580 is similar in structure to the wafer 400 in FIG. 4D. The membrane layer 552 in FIG. 5F is analogous to the membrane layer 412 in FIG. 4D. The membrane layer 552 is disposed directly on the substrate 500 in FIG. 5F similar to the membrane layer 412 that is disposed on the substrate 404 in FIG. 4D.

Figure 6C:
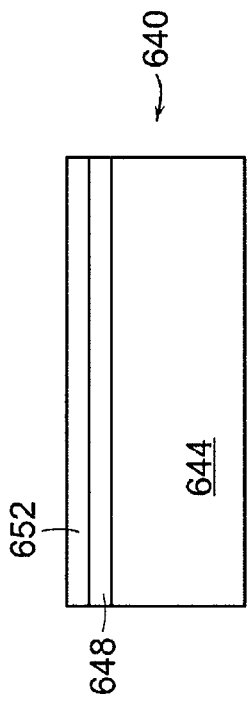
FIG. 6C is a schematic cross-sectional illustration of a second wafer.
Figure 6D:
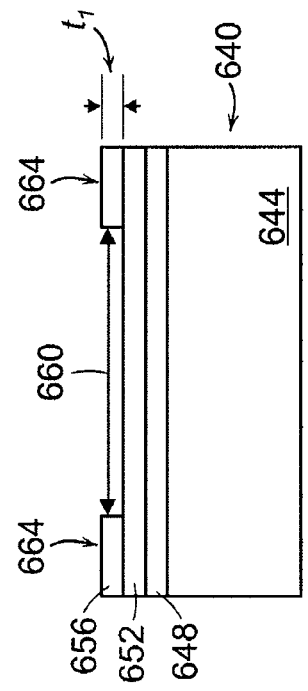
FIG. 6D is a schematic cross-sectional illustration of the wafer of FIG. 6C after deposition of a gap layer.
Figure 6A:
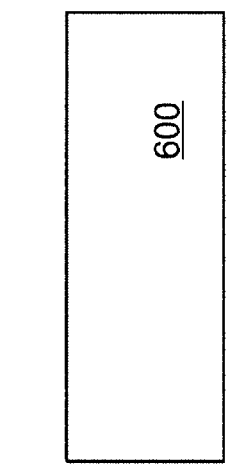
FIG. 6A is a schematic cross-sectional illustration of a wafer.
Figure 6B:
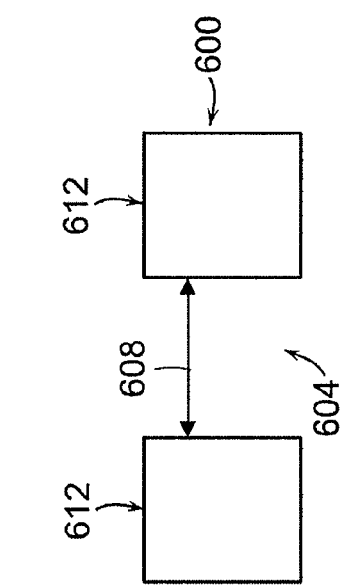
FIG. 6B is a schematic cross-sectional illustration of a cavity in the wafer of FIG. 6A.

FIGS. 6A-6F illustrate alternative steps for forming a membrane over a cavity involving bonding two layers together. Referring to FIG. 6A, a first wafer 600 is illustrated. FIG. 6B illustrates the first wafer 600 after a cavity 604 has been formed through the wafer 600. The cavity 604 can be formed according to the methods described herein previously (e.g., subsequent dry and wet removal processes). The cavity 604 defines a first opening 608, and the wafer 600 defines two surfaces 612 that can be prepared (e.g., by cleaning) for bonding with another wafer. As illustrated, the cavity 604 is substantially rectangular; however, other geometries are possible as well, for example, the trapezoidal geometry as described previously.

FIG. 6C illustrates a second wafer 640 that includes a substrate 644, an intermediate layer 648, and a membrane layer 652. In some embodiments, the second wafer 640 is an SOI wafer. FIG. 6D illustrates the second wafer 640 that has a gap layer 656 disposed on the membrane layer 652. The gap layer 656 defines a second opening 660. The second opening 660 can be formed according to the following steps. The gap layer 656 without the second opening 660 is deposited on the membrane layer 652 (e.g., a substantially uniformly deposited material). The gap layer 656 is deposited using known deposition techniques. A photoresist material (not shown) is patterned on the gap layer 656 to define an area (not shown) that is not masked by the photoresist material. The wafer 640 is subjected to a removal process that removes the portion of the gap layer 656 that defines the opening 660. The photoresist material is then removed from the wafer 640, leaving the gap layer 656 as depicted in FIG. 4D.

The gap layer 656 defines a thickness dimension $t_1$ that is defined and/or determined when the gap layer 656 is formed (e.g., during deposition or after the photoresist material has been removed). The thickness dimension $t_1$ can affect the size of the opening 660 as discussed above. For example, the size of the second opening 660 can exceed the size of the first opening 608 by an amount that is greater than the thickness $t_1$ of the intermediate portion (e.g., the gap layer 656). The gap layer 656 also includes two surfaces 664 that are prepared for bonding (e.g., by cleaning) to the surfaces 612 of first wafer 600.

Figure 6E:
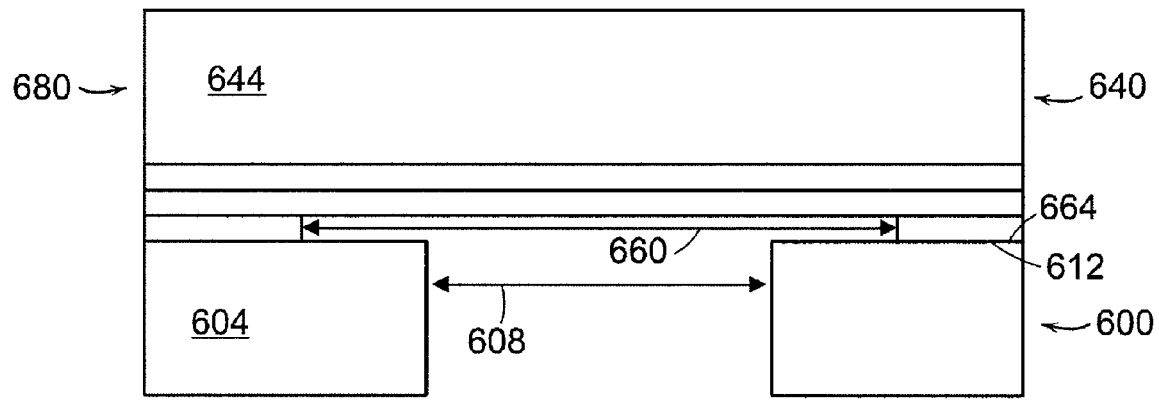
FIG. 6E is a schematic cross-sectional illustration of a composite wafer after the wafers of FIG. 6B and FIG. 6D have been bonded together.
Figure 6F:
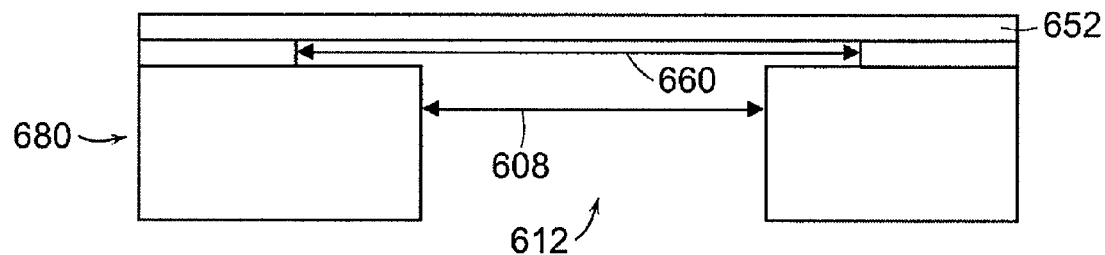
FIG. 6F is a schematic cross-sectional illustration of the composite wafer of FIG. 6E after a portion of the wafer of FIG. 6D has been removed.

FIG. 6E illustrates a composite wafer 680 that is formed by bonding the second wafer 640 to the first wafer 600. More particularly, the surfaces 664 of the gap layer 656 are bonded to the corresponding surfaces 612 of the first wafer 600 (e.g., using anodic or fusion bonding) as discussed above. The second wafer 640 is bonded to the first wafer 600 such that the second opening 660 is adjacent the first opening 608. The size of the second opening 660 exceeds the size of the first opening 604 by an amount according to a desired parameter. The desired parameter is associated with the performance of a device (not shown) employing the composite wafer 680. FIG. 6F illustrates the composite wafer 680 after the substrate 644 and the intermediate layer 648 of the second wafer 640 have been removed (e.g., by a removal process as discussed above). The composite wafer 680 includes the membrane 652 disposed over the second opening 660, the first opening 608, and the cavity 604. An integrated circuit (not shown) can be implanted or deposited on the membrane layer 652 (e.g., before or after the layer transfer).

Figure 7A:
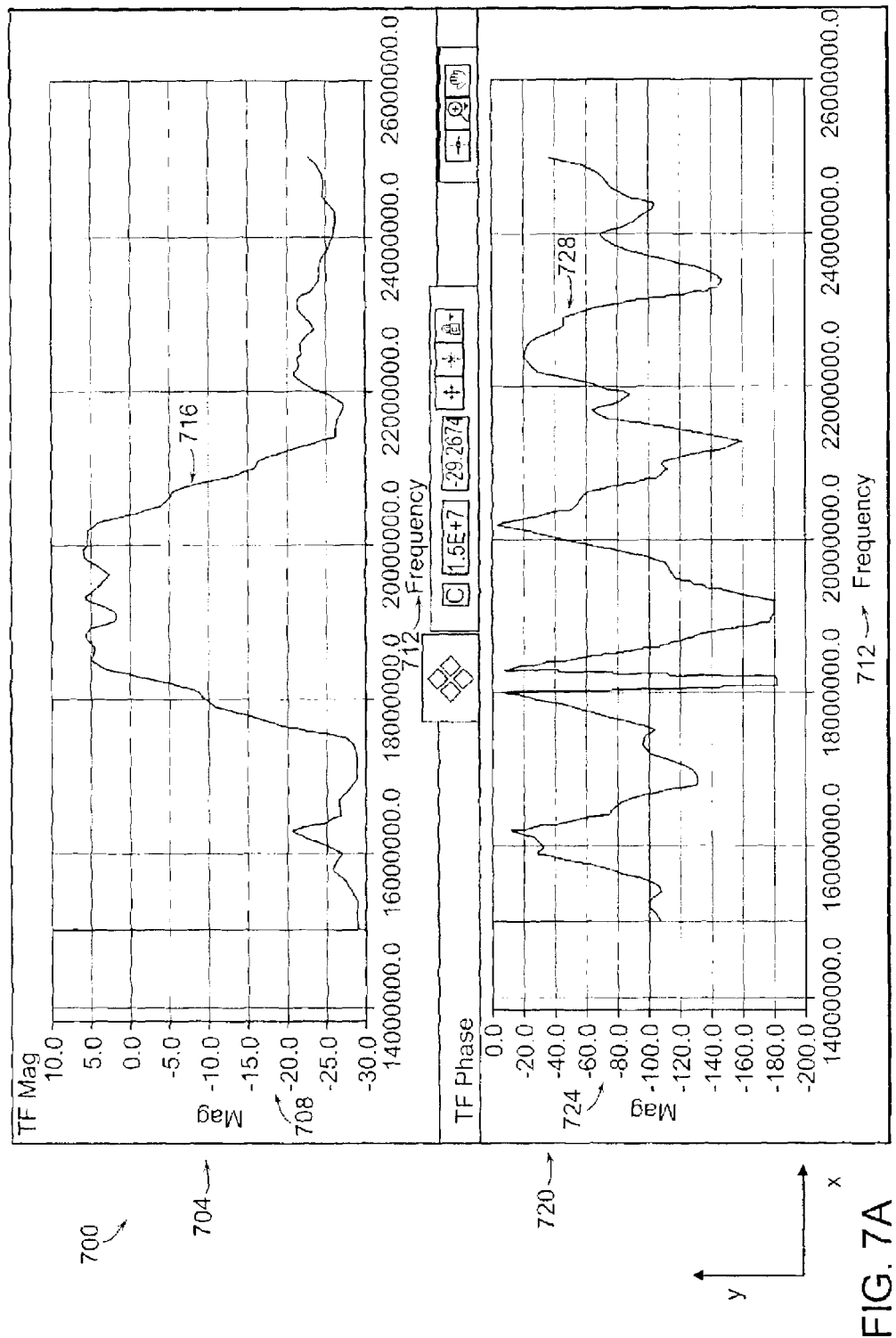
FIG. 7A is a graphical representation of the frequency response magnitude and phase versus frequency for a device not incorporating principles of the invention.

FIG. 7A is a graph 700 of the frequency response magnitude (704) and phase (720) measured during an experiment conducted using a device that does not incorporate principles of the invention. The device used to produce the graph 700 is a resonant device that did not employ a membrane with an undercut relative to a cavity of the device as illustrated in, for example, FIG. 1C. The resonant device was constructed from a silicon wafer using micro-fabrication techniques known in the art, for example, as described in U.S. patent application Ser. No. 11/183,484, which is incorporated herein by reference. A cavity is etched into the substrate to produce a thin, suspended membrane that is approximately 1.6 millimeters long, 0.4 millimeters wide and 2 micrometers thick. The overall substrate thickness is approximately 500 micrometers, so the depth of the cavity is just slightly less than the substrate thickness. A layer of aluminum nitride 0.5 micrometers thick is deposited over an outer surface (i.e., the surface opposite the cavity) of the membrane.

Electrode material in the form of two sets of interdigitated metal electrode material is deposited over an outer surface of the electrically responsive material. In some embodiments, titanium and/or gold are suitable electrode materials. In one embodiment, a 100 Angstrom-thick layer of titanium with an overlayer of 800 Angstrom-thick layer of gold is used as the electrode material.

A layer of metal (e.g., approximately 1000 Angstroms of gold with a 100 Angstrom titanium adhesion layer) is deposited on an inner surface (i.e., the surface facing the cavity) of the membrane to, for example, facilitate immobilization of capture agents. Biological or chemical matter binds to capture agents on the layer under circumstances where the device is used to quantify the matter in, for example, a fluid sample. In some embodiments, no layer of metal is used.

In operation, instrument/control electronics apply a time-varying electrical signal to one set of the electrode material to generate vibrations in the suspended membrane. The instrument/control electronics also monitor the vibrational characteristics of the membrane by receiving a sensor signal from the second set of electrode material.

A standing wave was established on the membrane by the instrument/control electronics, and the frequency response relating to the standing wave was measured. A fluid was interacted with the membrane, which provided a load on the membrane. The measured frequency response characteristics depend on the fluid properties. By monitoring changes in frequency response characteristics, one or more properties of the fluid can be determined. In other applications, changes in the resonance characteristics can be used to determine the presence or absence of a chemical or biological constituent in a sample or to quantify their amounts in a sample. The y-axis 708 of plot 704 is the magnitude of an output signal applied to the resonant device relative to an input signal of the resonant device. The x-axis 712 of plot 704 is frequency in Hertz (Hz). Curve 716 is the frequency response magnitude for a resonant device that does not incorporate principles of the invention. The y-axis 724 of plot 720 is the phase (e.g. phase slope) of an output signal applied to the resonant device relative to an input signal of the resonant device. The x-axis 712 of plot 720 is frequency in Hertz (Hz). Curve 728 is frequency response phase for the resonant device which does not incorporate principles of the invention. The relative maxima of the first curve 716 correspond to modes of oscillation of the device. These peaks correspond to regions of high phase slope of the second curve 728. In FIG. 7A, the modes of oscillation are poorly distinguished.

Figure 7B:
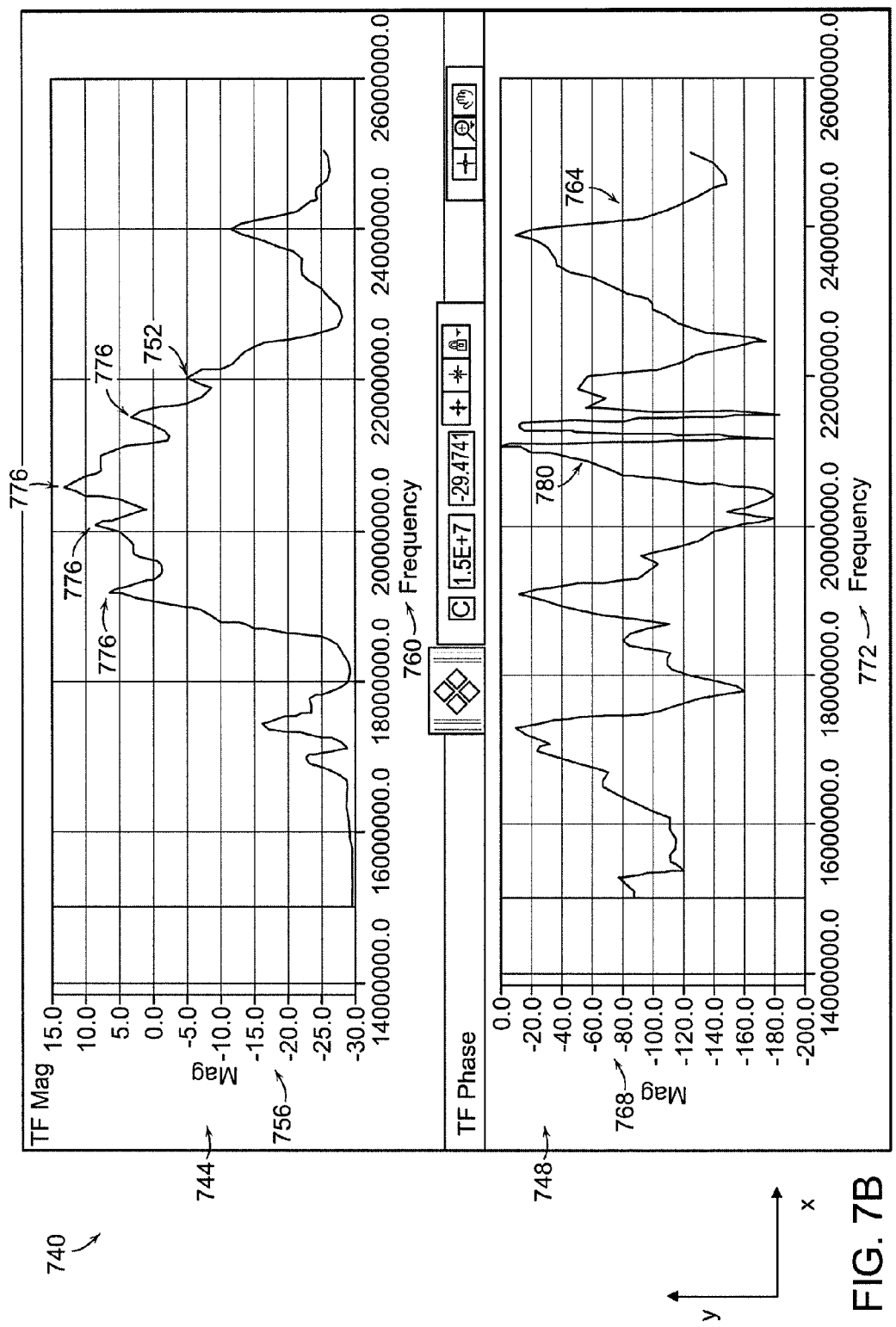
FIG. 7B is a graphical representation of the frequency response magnitude and phase versus frequency for a device incorporating principles of the invention.

FIG. 7B is a graph 740 of the frequency response magnitude (744) and phase (748) measured during an experiment conducted using a device that does incorporate principles of the invention. Curve 752 is the frequency response magnitude for a resonant device that does incorporate principles of the invention. The y-axis 756 of plot 744 is the magnitude of an output signal applied to the resonant device relative to an input signal of the resonant device. The x-axis 760 of plot 744 is frequency in Hertz (Hz). Curve 764 of FIG. 7B is the frequency response phase for the resonant device which does incorporate principles of the invention. The y-axis 768 of plot 748 is the phase (e.g. phase slope) of an output signal applied to the resonant device relative to an input signal of the resonant device. The x-axis 772 of plot 748 is frequency in Hertz (Hz).

The device used to produce the graph 740 was a resonant device that employed a membrane with an undercut of approximately 10 micrometers relative to the cavity (as illustrated in, for example, FIG. 1D). A standing wave was established on the membrane, and the frequency response relating to the standing wave was measured and is depicted on the graph 740. A fluid was interacted with the membrane, and the resonance characteristics again changed in response to the load provided by the fluid.

The first curve 752 maxima 776 (also called "peaks") in the range of frequency values are more distinct than those in curve 716, representing more isolated modes of oscillation of the device. The relative maxima 776 correspond closely to the regions of high phase slope 780 of the second curve 764 in the same bandwidth of frequency. The measured values of the phase slopes of curve 764 for these peaks are about twice that of similar peaks and regions of high phase slope of curves 716 and 728.

The device that incorporates the principles of the invention provides improved frequency response characteristics. The more distinct peaks 776 provide enhanced identification of the modes. Since the modes are more isolated, the response of an individual mode can be better discriminated. This has advantages for various sensing applications such as fluid property measurement as well as chemical and biological detection. The higher phase slope indicates that the device incorporating the invention operates with lower loss. This has advantages for both sensing and actuating applications. With lower loss, less input energy is required to achieve a given output. For sensing applications, the higher phase slope allows better detection sensitivity when employing phase tracking methods.

Figure 8A:
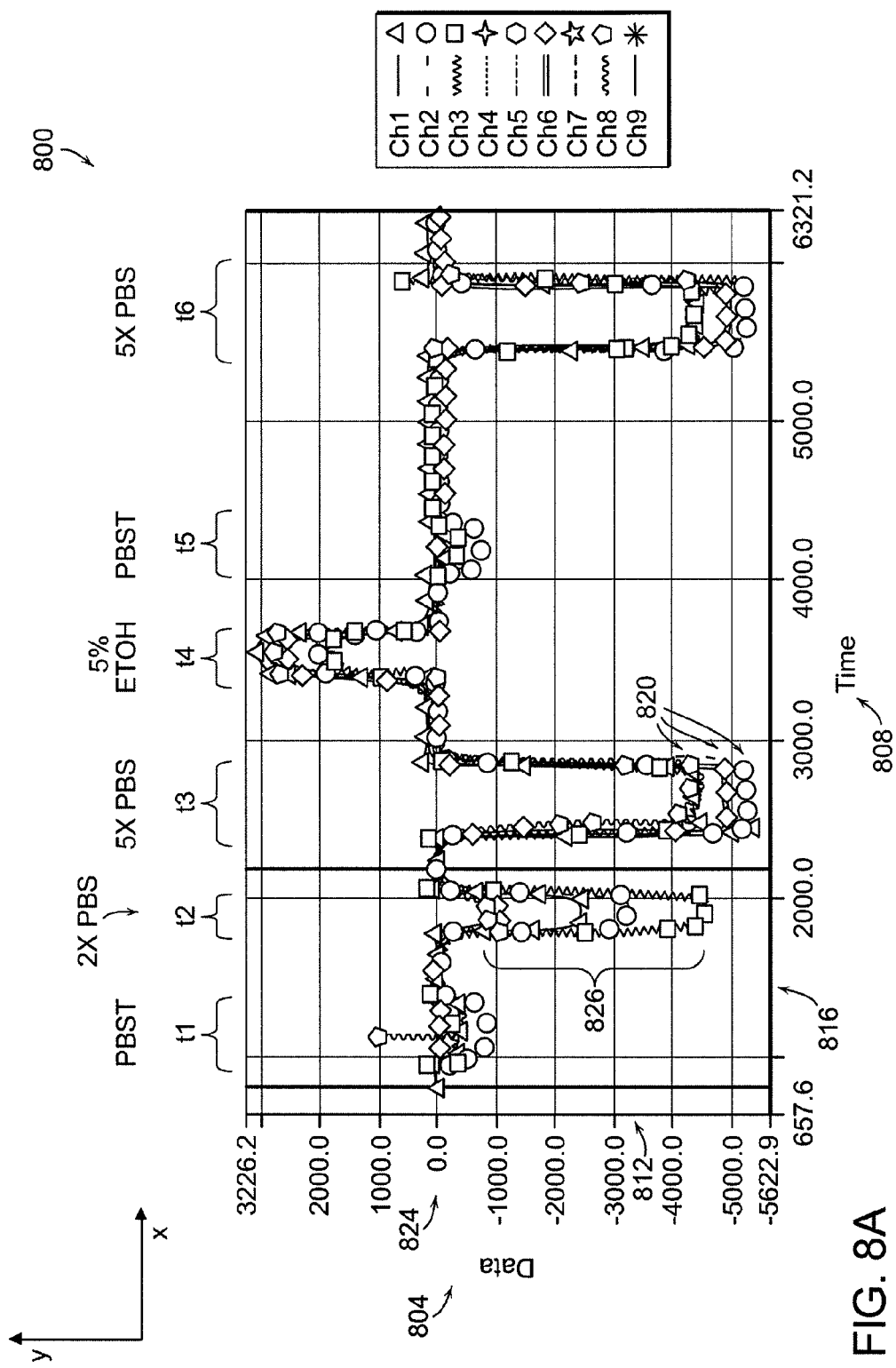
FIG. 8A is a graphical representation of a plot of data acquired versus time for a device not incorporating principles of the invention.
Figure 8B:
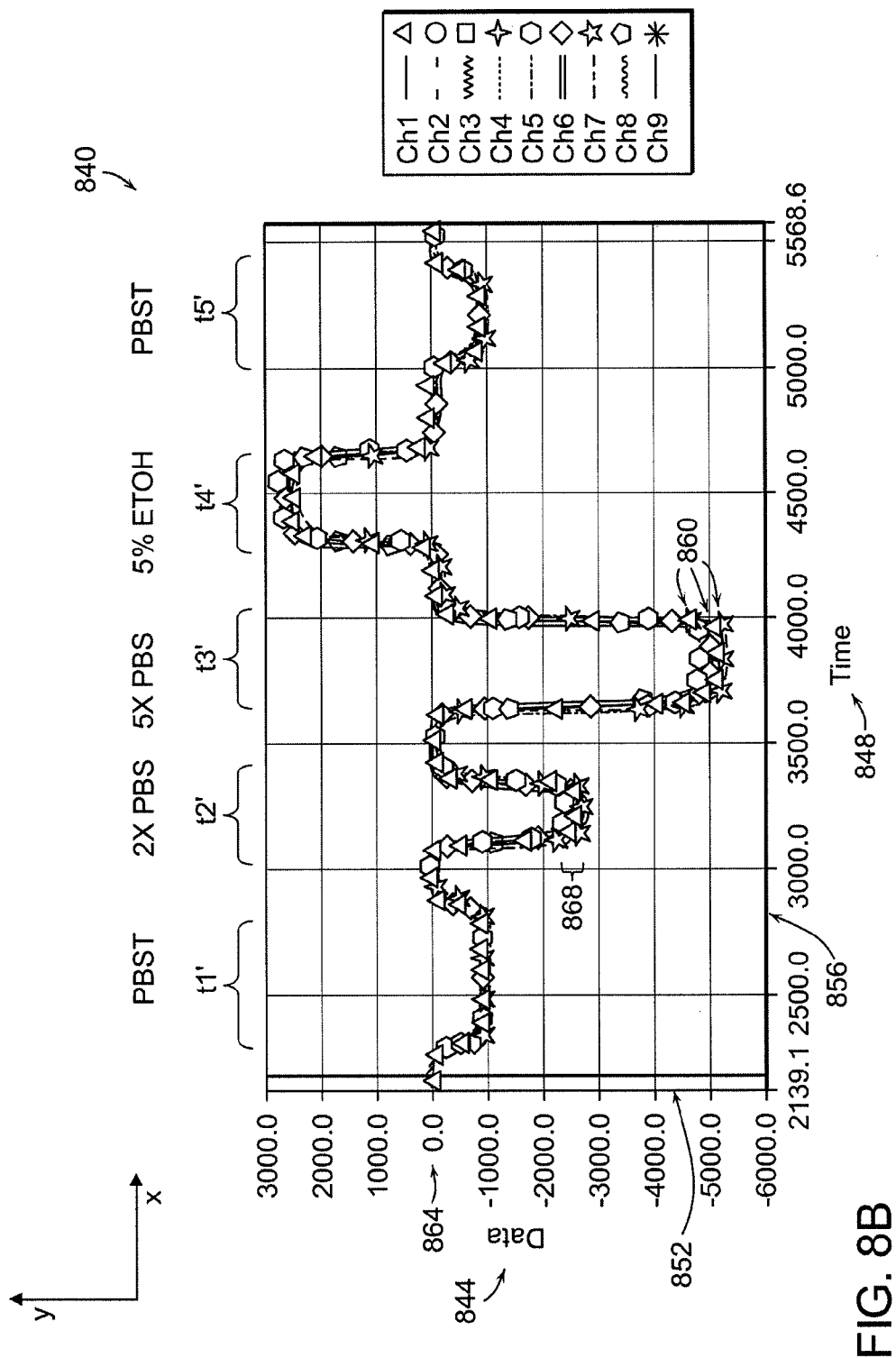
FIG. 8B is a graphical representation of a plot of data acquired versus time for a device incorporating principles of the invention.

Referring now to FIGS. 8A and 8B, tests were performed to characterize the response of flexural plate wave devices to fluids with differing properties. In these experiments, an initial frequency baseline was established in deionized water with 0.1% TERGITOL™ NP40 nonionic surfactant (The Dow Chemical Company, Michigan). Four other solutions were used to produce a sensor response relative to this baseline. A stock solution of 0.1 M phosphate buffered saline solution (also known as 10×PBS) was purchased from VWR International, catalog #EM-6505. A 5×PBS solution was made by mixing equal parts of 10×PBS and deionized water. A 2×PBS solution was made by mixing 1 part 10×PBS with 4 parts dionized water. A 1×PBS solution was made by mixing 1 part 10×PBS with 9 parts dionized water. A fourth solution comprised of 5% ethanol (200 proof) in deionized water (5% ETOH). The 5% ETOH, 1×PBS, 2×PBS and 5×PBS solutions were used to measure the device response relative to a baseline established in deionized water with 0.1% NP40.

FIG. 8A is a graphical representation of a plot 800 of data (804) acquired versus time (808) for a device not incorporating principles of the invention. The y-axis 812 of the plot 800 is the change in tracked frequency in units of parts per million (ppm) frequency change. The x-axis 816 of the plot 800 is time in units of seconds. The curves 820 on the plot 800 are plots of discrete data points of the experimental results associated with several flexural plate wave devices (e.g., resonant devices) tested that do not embody principles of the invention. In this experiment, a variety of fluids were introduced to contact a surface of the resonant devices (e.g., a surface of a membrane of the resonant devices). Each of the resonant devices outputs a signal that varies based on physical properties (e.g., density, viscosity, speed of sound in the fluid) of the fluid in contact with the surface of the resonant device.

In this experiment, an initial frequency baseline 824 was established in deionized water with 0.1% NP40. From about 1000 seconds to 1400 seconds (e.g., time t1), 1×PBS solution (referred to in FIG. 8A as PBST) was delivered to the surface of the resonant device before returning to deionized water with 0.1% NP40. 2×PBS was delivered to the surface of the resonant device from about 1800 seconds to about 2000 (e.g., time t2) seconds before returning to deionized water with 0.1% NP40. 5×PBS was delivered to the surface of the resonant device from about 2400 seconds to about 2800 (e.g., time t3) seconds before returning to deionized water with 0.1% NP40. 5% ETOH was delivered to the surface of the resonant device from about 3400 seconds to about 3700 seconds (e.g., time t4) before returning to deionized water with 0.1% NP40. The device was again exposed to 1×PBS (referred to in FIG. 8A as PBST) from 4000 seconds to 4400 seconds (e.g., time t5) before returning to deionized water with 0.1% NP40. The device was again exposed to 5×PBS from 5400 seconds to 5800 seconds (e.g., time t6) before returning to deionized water with 0.1% NP40.

FIG. 8B is a graphical representation of a plot 840 of data (844) acquired versus time (848) for a device incorporating principles of the invention. The y-axis 852 of the plot 840 is the change in tracked frequency in units of parts per million frequency change. The x-axis 856 of the plot 840 is time in units of seconds. The curves 860 are plots of discrete data points of the experimental results associated with several flexural plate wave devices (e.g., resonant devices) tested that embody principles of the invention. In this experiment, a variety of fluids were introduced to contact a surface of the resonant devices (e.g., a surface of a membrane). Each of the resonant devices outputs a signal that varies based on physical properties (e.g., density, viscosity, speed of sound in the fluid) of the fluid in contact with the surface of the resonant device.

The initial frequency baseline 864 was established in deionized water with 0.1% NP40. From about 2300 seconds to 2850 seconds (e.g., time t1'), 1×PBS solution (referred to as PBST in FIG. 8B) was delivered to the surface of the resonant device before returning to deionized water with 0.1% NP40. 2×PBS was delivered to the surface of the resonant device from about 3200 seconds to about 3350 seconds (e.g., time t2') before returning to deionized water with 0.1% NP40. 5×PBS was delivered to the surface of the resonant device from about 3600 seconds to about 4000 seconds (e.g., time t3') before returning to deionized water with 0.1% NP40. 5% ETOH was delivered to the surface of the resonant device from about 4300 seconds to about 4650 seconds (e.g., time t4') before returning to deionized water with 0.1% NP40. The device was again exposed to 1×PBS (referred to as PBST in FIG. 8B) from 5000 seconds to 5400 seconds (e.g., time t5') before returning to deionized water with 0.1% NP40.

For devices that embody principles of the invention, the frequency changes produced as a result of exposure to the fluid solutions have less variability. As shown in FIG. 8B, the frequency change produced by each device in response to exposure to the fluids varies by less than +/−10% from device to device. For example, the frequency change in response to 2×PBS (e.g., during time t2') ranges from −2300 ppm to −2700 ppm (868). In some embodiments, devices that do not include the principles of the invention are more variable. As shown in FIG. 8A, the frequency change in response to 2×PBS in this case ranges from −800 ppm to −4700 ppm (826). Increased variability is observed at the other fluid conditions (e.g., during the other enumerated time intervals t1 and t3-t6). The decreased variability of response afforded by the invention allows for lower manufacturing costs for devices produced using these methods. Since the distribution of responses is tighter, a higher yield in manufacturing can be achieved. Further, in some embodiments, the design of the signal processing electronics and software for the resonant devices can be simplified for both factory calibration and field operation because of the decreased variability in output response of the resonant devices. Fluid property sensing has broad applicability in industrial, medical and research applications.

In any of the above embodiments, a material layer, e.g., gold, can be deposited on the membrane and the walls of the cavity. This material layer facilitates the application of coatings that allow the surface properties to be modified for improved fluid flow through the cavity and along the membrane or for biofunctionalization of these surfaces. In some embodiments, a first material (not shown) is deposited on the cavity walls and a second, different material (not shown) is deposited on the membrane. Devices employing the concepts described above are suitable for a wide range of practical applications such as sensing, actuating, and pumping fluids. Properties and composition of the fluids can be determined based on the response of the frequency response of the device. Determining the presence or absence of chemical or biochemical components can be similarly determined. Furthermore, the amounts of these compounds can be quantified. Outputs of such systems include frequency responses and other signals capable of transmitting comparative information.

While the invention has been particularly shown and described with reference to specific embodiments, it should be understood by those skilled in the art that various changes in form and detail may be made therein without departing from the spirit and scope of the invention as defined by the appended claims.

What is claimed is:

1. A micro-fabricated fluidic sensing device comprising:
   a substrate defining a first cavity passing through the substrate, the cavity defining a first opening;
   an intermediate portion disposed over the substrate defining a second opening that is larger in size than the first opening, wherein the dimensions of the second opening are determined according to a performance parameter of the sensing device; and
   a membrane sensitive to properties of a fluid interacting with the membrane positioned adjacent the second opening.

2. The device of claim 1, wherein the dimensions of the second opening comprise at least one of a length dimension, a width dimension, a height dimension, or any combination thereof.

3. The device of claim 1, wherein the intermediate portion is formed of an intermediate layer disposed on the substrate material.

4. The device of claim 3, wherein the intermediate layer comprises an oxide material.

5. The device of claim 1, wherein the membrane comprises the intermediate portion.

6. The device of claim 1, wherein the membrane comprises at least one of silicon, polysilicon, silicon nitride, aluminum nitride, zinc oxide, aluminum, molybdenum, copper, gold, titanium, parylene, PMMA, SU-8, or any combination thereof.

7. The device of claim 1, wherein the membrane comprises two or more layers comprising one or more membrane materials.

8. The device of claim 1, wherein the size of the second opening is greater than the size of the first opening by an amount greater than about a thickness of the intermediate portion.

9. The device of claim 1, wherein the second opening is larger in size than the first opening by an amount greater than about two times a thickness of the intermediate portion.

10. The device of claim 1, wherein the second opening is larger than the first opening by an amount between about 5 and about 10 micrometers.

11. The device of claim 1, wherein the second opening is larger than the first opening by an amount between about 10 micrometers and about 30 micrometers.

12. The device of claim 1, wherein the intermediate portion has a thickness of about 1 micrometer.

13. The device of claim 1, wherein the size of the membrane is determined based at least in part on the size of the second opening.

14. The device of claim 1, wherein the membrane cooperates with the second opening to form a boundary associated with a boundary condition and the size of the membrane is determined based at least in part on the boundary condition.

15. The device of claim 1, wherein the membrane comprises a plate structure.

16. The device of claim 1, further comprising:
   an electroactive layer disposed on a surface of the membrane; and
   a set of electrodes disposed on a surface of the electroactive layer.

17. The device of claim 16, wherein the electroactive layer comprises a piezoelectric material.

18. The device of claim 1, wherein the cavity cooperates with the membrane to form a fluid path.

19. The device of claim 1, wherein the parameter of the device comprises at least one of sensitivity, accuracy, operational lifetime, or any combination thereof.

20. The device of claim 1, wherein the parameter of the device comprises frequency response.

21. The device of claim 15, wherein the sensing device is a flexural plate wave device.

22. A micro-fabricated fluidic resonant sensing device comprising:
   a substrate defining a first cavity passing through the substrate, the cavity defining a first opening;
   an intermediate layer disposed over the substrate defining a second opening that is larger in size than the first opening, wherein a thickness of the intermediate layer determines a height of the second opening; and
   a membrane sensitive to properties of a fluid interacting with the membrane positioned adjacent the second opening.

* * * * *